(12) United States Patent
Bowles et al.

(10) Patent No.: US 9,012,224 B2
(45) Date of Patent: Apr. 21, 2015

(54) CHIMERIC VECTORS

(75) Inventors: Dawn E. Bowles, Durham, NC (US);
Chengwen Li, Chapel Hill, NC (US);
Joseph E. Rabinowitz, Secane, PA
(US); Josh Grieger, Chapel Hill, NC
(US); Mavis Agbandje-McKenna,
Gainesville, FL (US); **Richard Jude
Samulski**, Chapel Hill, NC (US)

(73) Assignees: **The University of North Carolina at
Chapel Hill, Chapel Hill, NC (US); The
University of Florida Research
Foundation**, Gainesville, FL (US)

( * ) Notice: Subject to any disclaimer, the term of this patent is extended or adjusted under 35 U.S.C. 154(b) by 1145 days.

(21) Appl. No.: 12/983,547

(22) Filed: Jan. 3, 2011

(65) Prior Publication Data

US 2011/0104119 A1    May 5, 2011

Related U.S. Application Data

(63) Continuation of application No. 11/793,430, filed as application No. PCT/US2005/045552 on Dec. 15, 2005, now Pat. No. 7,892,809.

(60) Provisional application No. 60/636,126, filed on Dec. 15, 2004.

(51) Int. Cl.
*C12N 15/861* (2006.01)
*C12N 15/86* (2006.01)

(52) U.S. Cl.
CPC ...... *C12N 15/86* (2013.01); *C12N 2750/14122* (2013.01); *C12N 2750/14143* (2013.01); *C12N 2750/14144* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 5,436,146 A | 7/1995 | Shenk et al. |
| 5,478,745 A | 12/1995 | Samulski et al. |
| 5,589,377 A | 12/1996 | Lebkowski et al. |
| 5,622,856 A | 4/1997 | Natsoulis |
| 5,658,785 A | 8/1997 | Johnson |
| 5,681,731 A | 10/1997 | Lebkowski et al. |
| 5,753,500 A | 5/1998 | Shenk et al. |
| 5,756,283 A | 5/1998 | Wilson et al. |
| 5,773,289 A | 6/1998 | Samulski et al. |
| 5,780,280 A | 7/1998 | Lebkowski et al. |
| 5,780,447 A | 7/1998 | Nienhuis |
| 5,786,211 A | 7/1998 | Johnson |
| 5,834,441 A | 11/1998 | Philip et al. |
| 5,843,742 A | 12/1998 | Natsoulis et al. |
| 5,846,528 A | 12/1998 | Podsakoff et al. |
| 5,846,546 A | 12/1998 | Hurwitz et al. |
| 5,856,152 A | 1/1999 | Wilson et al. |
| 5,858,351 A | 1/1999 | Podsakoff et al. |
| 5,858,775 A | 1/1999 | Johnson |
| 5,861,171 A | 1/1999 | Philip et al. |
| 5,861,314 A | 1/1999 | Philip et al. |
| 5,863,541 A | 1/1999 | Samulski et al. |
| 5,866,552 A | 2/1999 | Wilson et al. |
| 5,866,696 A | 2/1999 | Carter et al. |
| 5,869,305 A | 2/1999 | Samulski et al. |
| 5,871,982 A | 2/1999 | Wilson et al. |
| 5,872,005 A | 2/1999 | Wang et al. |
| 5,874,304 A | 2/1999 | Zolotukhin et al. |
| 5,874,556 A | 2/1999 | Lupton et al. |
| 5,882,652 A | 3/1999 | Valdes et al. |
| 5,905,040 A | 5/1999 | Mazzara et al. |
| 5,916,563 A | 6/1999 | Young et al. |
| 5,922,315 A | 7/1999 | Roy |
| 5,945,335 A | 8/1999 | Colosi |
| 5,952,221 A | 9/1999 | Kurtzman et al. |
| 5,962,274 A | 10/1999 | Parks |
| 5,962,313 A | 10/1999 | Podsakoff et al. |
| 6,001,371 A | 12/1999 | Young et al. |
| 6,156,303 A | 12/2000 | Russell et al. |
| 6,468,524 B1 | 10/2002 | Chiorini et al. |
| 6,468,771 B1 | 10/2002 | Einerhand et al. |
| 6,491,907 B1 | 12/2002 | Rabinowitz |
| 6,759,237 B1 | 7/2004 | Wilson et al. |
| 6,984,517 B1 | 1/2006 | Chiorini et al. |

(Continued)

FOREIGN PATENT DOCUMENTS

| | | |
|---|---|---|
| AU | 199942205 | 6/2003 |
| WO | WO 95/28493 | 10/1995 |

(Continued)

OTHER PUBLICATIONS

Weinberg et al., Neuropharmacology vol. 69 (2013) pp. 82-88.*
Rodino-Klapac et al., Curr Neurol Neurosci Rep vol. 13 (2013) p. 332.*
Ortolano et al., Recent Patents on Endocrine, Metabolic & Immune Drug Discovery vol. 6 (2012) pp. 47-66.*
Agbandje et al., "Structure Determination of Feline Panleukopenia Virus Empty Particles" *Proteins: Structure, Function, and Genetics* 16:155-171 (1993).
Alexander et al., "Transfer of Contaminants in Adeno-Associated Virus Vector Stocks Can Mimic Transduction and Lead to Artifactual Results" *Human Gene Therapy* 8:1911-1920 (Nov. 1, 1997).
Anderson, "Human Gene Therapy," *Nature* 392: 25-30 (1998).

(Continued)

*Primary Examiner* — Jim Ketter
(74) *Attorney, Agent, or Firm* — Myers Bigel Sibley & Sajovec, P.C.

(57) ABSTRACT

The present invention is based, in part, on the discovery that parvovirus (including AAV) capsids can be engineered to incorporate small, selective regions from other parvoviruses that confer desirable properties. The inventors have discovered that in some cases as little as a single amino acid insertion or substitution from a first parvovirus (e.g., an AAV) into the capsid structure of another parvovirus (e.g., an AAV) to create a chimeric parvovirus is sufficient to confer one or more of the desirable properties of the first parvovirus to the resulting chimeric parvovirus and/or to confer a property that is not exhibited by the first parvovirus or is present to a lesser extent.

15 Claims, 14 Drawing Sheets

(56) References Cited

U.S. PATENT DOCUMENTS

| | | | |
|---|---|---|---|
| 7,172,893 | B2 | 2/2007 | Rabinowitz et al. |
| 7,252,997 | B1 | 8/2007 | Hallek et al. |
| 7,259,151 | B2 | 8/2007 | Arbetman et al. |
| 2003/0215422 | A1 | 11/2003 | Chiorini et al. |
| 2004/0057931 | A1 | 3/2004 | Wilson et al. |
| 2004/0057932 | A1 | 3/2004 | Wilson et al. |
| 2004/0057933 | A1 | 3/2004 | Wilson et al. |
| 2004/0086490 | A1 | 5/2004 | Chiorini et al. |
| 2005/0255089 | A1 | 11/2005 | Chiorini et al. |
| 2006/0188483 | A1 | 8/2006 | Rabinowitz et al. |
| 2006/0188484 | A1 | 8/2006 | Rabinowitz et al. |

FOREIGN PATENT DOCUMENTS

| | | |
|---|---|---|
| WO | WO 96/00587 | 1/1996 |
| WO | WO96/36364 | 11/1996 |
| WO | WO 97/05266 | 2/1997 |
| WO | WO 97/38723 | 10/1997 |
| WO | WO 98/09524 | 3/1998 |
| WO | WO 98/11244 | 3/1998 |
| WO | WO 98/32842 | 7/1998 |
| WO | WO 98/41240 | 9/1998 |
| WO | WO 99/61601 | 12/1999 |
| WO | WO 99/67393 | 12/1999 |
| WO | WO 00/28004 | 5/2000 |
| WO | WO 00/28061 | 5/2000 |
| WO | WO 01/05991 | 1/2001 |
| WO | WO 01/05990 | 2/2001 |
| WO | WO 01/68888 A2 | 9/2001 |
| WO | WO 01/68888 A3 | 9/2001 |
| WO | WO 01/83692 | 11/2001 |

OTHER PUBLICATIONS

Antonietti et al.; "Characterization of the Cell Type-Specific Determinant in the Genome of Minute Virus of Mice," *Journal of Virology* 62:2 552-557 (Feb. 1988).

Ball-Goodrich et al.; Two Amino Acid Substitutions within the Capsid Are Coordinately Required for Acquisition of Fibrotropism by the Lymphotropic Strain of Minute Virus of Mice, *Journal of Virology* 66:6 3415-3423 (Jun. 1992).

Bartlett et al., "Genetics and Biology of Adeno-Associated Virus," *Viral Vectors* 55-73 (1995).

Bloom et al., "Characterization of Chimeric Full-Length Molecular Clones of Aleutian Mink Disease Parvovirus (ADV): Identification of a Determinant Governing Replication of ADV in Cell Culture," *Journal of Virology*: 5976-5988 (Oct. 1993).

Bowles et al., "Marker Rescue of Adeno-Associated Virus (AAV) Capsid Mutants: a Novel Approach for Chimeric AAV Production", Journal of Virology, vol. 77:1, pp. 423-432 (Jan. 2003). XP002975999.

Brown et al.; Chimeric Parvovirus B19 Capsids for the Presentation of Foreign Epitopes, *Virology* 198 477-488 (1994).

Burger et al., "Recombinant AAV Viral Vectors Pseudotyped with Viral Capsids from Serotypes 1,2, and 5 Display Differential Efficiency and Cell Tropism after Delivery to Different Regions of the Central Nervous System", Molecular Therapy, vol. 10:2, pp. 302-317 (Aug. 2004). XP004552211.

Chang et al.; Multiple Amino Acids in the Capsid Structure of Canine Parvovirus Coordinately Determine the Canine Host Range and Specific Antigenic and Hemagglutination Properties, *Journal of Virology* 66:12 6858-6867 (Dec. 1992).

Chapman et al.; Structure, Sequence, and Function Correlations Among Parvoviruses, Virology 194:491-508 (1993).

Chiorini et al.; Adeno-Associated Virus (AAV) Type 5 Rep Protein Cleaves a Unique Terminal Resolution Site Compared with Other AAV Serotypes, *Journal of Virology* 73:5 4293-4298 (May 1999).

Chiorini et al.; Cloning and Characterization of Adeno-Associated virus Type 5, *Journal of Virology* 73:2 1309-1319 (Feb. 1999).

Chiorini et al.; Cloning of Adeno-Associated Virus Type 4 (AAV4) and Generation of Recombinant AAV4 Particles, *Journal of Virology* 71:9 6823-6833 (Sep. 1997).

Conway et al., "Recombinant Adeno-Associated Virus Type 2 Replication and Packaging Is Entirely Supported by a Herpes Simplex Virus Type 1 Amplicon Expressing Rep and Cap," *Journal of Virology* 71:11 8780-8789 (Nov. 1997).

Dang et al. Gene therapy and translational cancer research. Clin. Can. Res. 5:471-474, 1999.

Douar et al. "Deleterious effect of peptide insertions in a permissive site of the AAV2 capsid" *Virology* 309:203-208 (2003).

Du et al., "Differential Myocardial Gene Delivery by Recombinant Serotype-Specific Adeno-associated Viral Vectors", Molecular Therapy, vol. 10:3, pp. 604-608 (Sep. 2004). XP004660600.

Extended European Search Report and Search Opinion (8 pages) corresponding to European Application No. 05826631.3; Dated: Mar. 30, 2009.

Faust et al. "Universal purification of AAV serotypes 1-5 modified to contain a heparin binding epitope" *Molecular Therapy* 9:S36-S36 (2004).

Fu et al.; Viral sequences enable efficient and tissue-specific expression of transgenes in *Xenopus, Nature Biotechnology* 16 253-257 (Mar. 1998).

Gao et al., "Clades of Adeno-Associated Viruses Are Widely Disseminated in Human Tissues," *Journal of Virology* 78:12 6381-6388 (Jun. 2004).

Gao et al., "Novel adeno-associated viruses from rhesus monkeys as vectors for human gene therapy," *PNAS* 99:18 11854-11859 (Sep. 3, 2002).

Gao et al.; *High-Titer Adeno-Associated Viral Vectors from a Rep/Cap Cell Line and Hybrid Shuttle Virus*, Human Gene Therapy 9:2353-2362 (Nov. 1, 1998).

Gardiner et al.; "Mapping of the Fibrotropic and Lymphotropic Host Range Determinants of the Parvovirus Minute Virus of Mice," *Journal of Virology* 62:8 2605-2613 (Aug. 1988).

Girod et al.; Genetic capsid modifications allow efficient re-targeting of adeno-associated virus type 2, *Nature Medicine* 5:9 1052-1056 (Sep. 1999).

Goldman et al.; Targeted Gene Delivery to Kaposi's Sarcoma Cells *via* the Fibroblast Growth Factor Receptor, *Cancer Research* 57 1447-1451 (Apr. 15, 1997).

Hauck et al., "Characterization of Tissue Tropism Determinants of Adeno-Associated Virus Type 1," *Journal of Virology* 77:4 2768-2774 (Feb. 2003).

Hermonat et al.; Genetics of Adeno-Associated Virus: Isolation and Preliminary Characterization of Adeno-Associated Virus Type 2 Mutants, *Journal of Virology* 51:2 329-339 (Aug. 1984).

Hodgson, C.P. Advances in vector systems for gene therapy. Exp. Opin. Ther. Patents 5:459-468, 1995.

Horiuchi et al.; *Mapping of Determinants of the Host Range for Canine Cells in the Genome of Canine Parvovirus Using Canine Parvovirus/Mink Enteritis Virus Chimeric Viruses*, Journal of General Virology 75:1319-1328 (1994).

Li et al.; Role for Highly Regulated *rep* Gene Expression in Adeno-Associated Virus Vector Production, *Journal of Virology* 71:7 5236-5243 (Jul. 1997).

Lieber et al., "AAV display-homing in on the target," *Nature Biotechnology* 21:9 1011-1013 (Sep. 2003).

Llamas-Saiz et al., "Structure Determination of Minute Virus of Mice" *Acta Crysta* D53 93-102 (1997).

Marshall, E. Gene therapy's growing pains. Science 269:1050-1055, 1995.

Maxwell et al.; Targeting a Feline Parvovirus to Human Tumor Cells (abstract), Cold Spring Harbor Laboratory, Vector Targeting Strategies for Therapeutic Gene Delivery meeting (Mar. 11-14, 1999) p. 87.

McCarty et al., "Integration of Adeno-Associated Virus (AAV) and Recombinant AAV Vectors," *Annu. Rev. Genet.* 38:819-45 (2004).

Miyamura et al.; Parvovirus particles as platforms for protein presentation, *Proc. Natl. Acad. Sci. USA* 91 8507-8511 (Aug. 1994).

Moskalenko et al.; Epitope Mapping of Human Anti-Adeno-Associated Virus Type 2 Neutralizing Antibodies: Implications for Gene Therapy and Virus Structure, *Journal of Virology* 74:4 1761-1766 (Feb. 2000).

Muller et al., "Random peptide libraries displayed on adeno-associated virus to select for targeted gene therapy vectors" Nature Biotechnology 21:9 1040-1046 (Sep. 2003).

(56) References Cited

OTHER PUBLICATIONS

Muralidhar et al.; Site-Directed Mutagenesis of Adeno-Associated Virus Type 2 Structural Protein Initiation Codons: Effects on Regulation of Synthesis and Biological Activity, *Journal of Virology* 68:1 170-176 (Jan. 1994).
Muramatsu et al.; Nucleotide Sequencing and Generation of an Infectious Clone of Adeno-Associated Virus 3, *Virology* 221 208-217 (1996).
Parrish et al.; "Canine Host Range and a Specific Epitope Map along with Variant Sequences in the Capsid Protein Gene of Canine Parvovirus and Related Feline, Mink, and Raccoon Parvoviruses," *Virology* 166:293-307 (1988).
Parrish et al.; "Rapid Antigenic-Type Replacement and DNA Sequence Evolution of Canine Parvovirus," *Journal of Virology* 65:12 6544-6552 (Dec. 1991).
Ponnazhagan et al.; Recombinant Human Parvovirus B19 Vectors: Erythroid Cell-Specific Delivery and Expression of Transduced Genes, *Journal of Virology* 72:6 5224-5230 (Jun. 1998).
Rabinowitz et al., "Cross-Dressing the Virion: the Transcapsidation of Adeno-Associated Virus Serotypes Functionally Defines Subgroups", Journal of Virology, vol. 78:9, pp. 4421-4432 (May 2004). XP002519618.
Rabinowitz et al., "Insertional Mutagenesis of AAV2 Capsid and the Production of Recombinant Virus," *Virology* 265: 274-285 (1999).
Rabinowitz et al.; *Adeno-Associated Virus Expression Systems for Gene Transfer*, Current Opinion in Biotechnology 9:5 470-475 (Oct. 1998).
Rabinowitz et al.; Targeted Adeno-Associated Virus (abstract), Cold Spring Harbor Laboratory, Vector Targeting Strategies for Therapeutic Gene Delivery meeting (Mar. 11-14, 1999) p. 82.
Romano et al. Latest developments in gene transfer technology: Achievements, perspectives, and controversies over therapeutic applications. Stem cells 18:19-39, 2000.
Ruffing et al.; Mutations in the carboxy terminus of adeno-associated virus 2 capsid proteins affect viral infectivity: lack of an RGD integrin-binding motif, *Journal of General Virology* 75 3385-3392 (1994).
Rutledge et al.; Infectious Clones and Vectors Derived from Adeno-Associated Virus (AAV) Serotypes Other Than AAV Type 2, *Journal of Virology* 72:1 309-319 (Jan. 1998).
Sedlik et al.; Recombinant parvovirus-like particles as an antigen carrier: A novel nonreplicative exogenous antigen to elicit protective antiviral cytotoxic T cells, *Proc. Natl. Acad. Sci, USA* 94 7503-7508 (Jul. 1997).
Simpson et al, "The Structure of an insect parvovirus (*Galleria mellonella* densovirus) at 3.7 A resolution" *Structure* 6:11 1355-1367 (1998).
Smuda et al.; Adeno-Associated Viruses Having Nonsense Mutations in the Capsid Genes: Growth in Mammalian Cells Containing an Inducible Amber Suppressor, *Virology* 184 310-318 (1991).

Spitzer et al., "Tropic determinant for canine parvovirus and feline panleukopenia virus functions through the capsid protein VP2," *Journal of General Virology* 78: 925-928 (1997).
Spitzer et al.; Species specificity for transduction of cultured cells by a recombinant LuIII roden parvovirus genome encapsidated by canine parvovirus or feline panleukopenia virus, *Journal of General Virology* 77 1787-1792 (1996).
Srivastava et al.; Construction of a recombinant human parvovirus B19: Adeno-associated virus 2 (AAV) DNA inverted terminal repeats are functional in an AAV-B19 hybrid virus, *Proc. Natl. Acad. Sci. USA* 86 8078-8082 (Oct. 1989).
Tsao et al.; "The Three-Dimensional Structure of Canine Parvovirus and Its Functional Implications," *Science* 251:1456-1464 (Mar. 22, 1991).
Urabe et al., "Insect Cells as a Factory to Produce Adeno-Associated Virus Type 2 Vectors," *Human Gene Therapy* 13:1935-1943 (Nov. 1, 2002).
Verma et al. Gene therapy-promises, problems and prospects. Nature 389:239-242, 1997.
Wang et al., "Recombinant AAV serotype 1 transduction efficiency and tropism in the murine brain," *Gene Therapy* 10, 1528-1534 (2003).
Wang et al., "Rescue and Replication of Adeno-Associated Virus Type 2 as well as Vector DNA Sequences from Recombinant Plasmids Containing Deletions in the Viral Inverted Terminal Repeats: Selective Encapsidation of Viral Genomes in Progeny Virions" *J. Virol.* 70(3):1668-1667 (1996).
Warrington et al., "Adeno-Associated Viruses Type 2 VP2 Capsid Protein Is Nonessential and Can Tolerate Large Peptide Insertions at Its N Terminus" *Journal of Virology* 78:12 6595-6609 (Jun. 2004).
Wu et al., "The Canine Parvovirus Empty Capsid Structure" *J. Mol. Biol.* 233: 231-244 (1993).
Wu et al., "Mutational Analysis of the Adeno-Associated Virus Type 2 (AAV2) Capsid Gene and Construction of AAV2 Vectors with Altered Tropism", Journal of Virology, vol. 74:18, pp. 8635-8647 (Sep. 2000). XP001028219.
Xiao et al., "Gene Therapy Vectors Based on Adeno-Associated Virus Type 1," *Journal of Virology* 73(5): 3994-4003 (May 1999).
Xiao et al.; Efficient Long-Term Gene Transfer into Muscle Tissue of Immunocompetent Mice by Adeno-Associated Virus Vector, *Journal of Virology* 70:11 8098-8108 (Nov. 1996).
Xiao et al,; Production of high-titer recombinant adeno-associated virus vectors in the absence of helper adenovirus, *J. Virol.* 72:3 2224 (15 pp.) (Mar. 1998).
Yang et al., "Virus-Mediated Transduction of Murine Retina with Adeno-Associated Virus: Effects of Viral Capsid and Genome Size," *Journal of Virology* 76:15 7651-7660 (Aug. 2002).
Yang et al.; Development of Novel Cell Surface CD34-Targeted Recombinant Adenoassociated Virus Vectors for Gene Therapy, *Human Gene Therapy* 9 1929-1937 (Sep. 1, 1998).
Japanese Patent Application No. 2007-546926, filed Apr. 20, 2009; Office Action mailed Aug. 16, 2011.

\* cited by examiner

```
AAV1    1   MAADGYLPDWLEDNLSEGIREWWDLKPGAPKPKANQQKQDDGRGLIVLPGYKYLGPFNGLDKGEPVNAADA
AAV2        MAADGYLPDWLEDTLSEGIRQWWKLKPGPPPPKPAERHKDDSRGLVLPGYKYLGPFNGLDKGEPVNEADA
            1         10        20        30        40        50        60        70

AAV1    71  AALEHDKAYDQQLKAGDNPYLRYNHADAEFQERLQEDTSFGGNLGRAVFQAKKRVLEPLGLVEEGAKTAP
AAV2        AALEHDKAYDRQLDSGDNPYLKYNHADAEFQERLKEDTSFGGNLGRAVFQAKKRVLEPLGLVEEPVKTAP
            71        80        90        100       110       120       130       140

AAV1    141 GKKRPVEQSPQEPDSSSGIGKTGQQPAKKRLNFGQTGDSESVPDPQPLGEPPATPAAVGPTTMASGGAP
AAV2        GKKRPVEHSPVEPDSSSGTGKAGQQPARKRLNFGQTGDADSVPDPQPLGQPPAAPSGLGTNTMATGSGAP
            141       150       160       170       180       190       200       210

AAV1    211 MADNNEGADGVGNASGNWHCDSTWLGDRVITTSTRTWALPTYNNHLYKQISSASTGASNDNHYFGYSTPW
AAV2        MADNNEGADGVGNSSGNWHCDSTWMGDRVITTSTRTWALPTYNNHLYKQISSQSGA-SNDNHYFGYSTPW
            211       220       230       240       250       260       270       280

AAV1    281 GYFDFNRFHCHFSPRDWQRLINNNWGFRPKRLNFKLFNIQVKEVTTNDGVTTIANNLTSTVQVFSDSEYQ
AAV2        GYFDFNRFHCHFSPRDWQRLINNNWGFRPKRLNFKLFNIQVKEVTQNDGTTTIANNLTSTVQVFTDSEYQ
            281       290       300       310       320       330       340       350

AAV1    351 LPYVLGSAHQGCLPPFPADVFMVPQYGYLTLNNGSQAVGRSSFYCLEYFPSQMLRTGNNFTFSYTFEEVP
AAV2        LPYVLGSAHQGCLPPFPADVFMVPQYGYLTLNNGSQAVGRSSFYCLEYFPSQMLRTGNNFTFSYTFEDVP
            351       360       370       380       390       400       410       420

AAV1    421 FHSSYAHSQSLDRLMNPLIDQYLYYLNRTQNQSGSAAQNKDLLFSRGSPAGMSVQPKNWLPGPCYRQQRV
AAV2        FHSSYAHSQSLDRLMNPLIDQYLYYLSRTNTPSGTTTTQSRLQFSQAGASDIRDQSRNWLPGPCYRQQRV
            421       430       440       450       460       470       480       490

AAV1    491 SKTKTDNNNSNFTWTGASKYNLNGRESIINPGTAMASHKDDEDKFFPMSGVMIFGKESAGASNTALDNVM
AAV2        SKTSADNNNSEYSWTGATKYHLNGRDSLVNPGPAMASHKDDEEKFFPQSGVLIFGKQGSEKTNVDIEKVM
            491       500       510       520       530       540       550       560

AAV1    561 ITDEEEIKATNPVATERFGTVAVNFQSSSTDPATGDVHAMGALPGMVWQDRDVYLQGPIWAKIPHTDGHF
AAV2        ITDEEEIRTTNPVATEQYGSVSTNLQRGNRQAATADVNTQGVLPGMVWQDRDVYLQGPIWAKIPHTDGHF
            561       570       580       590       600       610       620       630

AAV1    631 HPSPLMGGFGLKNPPPQLLIKNTPVPANPPAEFSATKFASFITQYSTGQVSVEIEWELQKENSKRWNPE
AAV2        HPSPLMGGFGLKHPPPQILIKNTPVPANPSTTFSAAKFASFITQYSTGQVSVEIEWELQKENSKRWNPE
            631       640       650       660       670       680       690       700

AAV1    701 VQYTSNYAKSANVDFTVDNNGLYTEPRPIGTRYLTRPL
AAV2        IQYTSNYNKSVNVDFTVDTNGVYSEPRPIGTRYLTRNL
            701       710       720       730
```

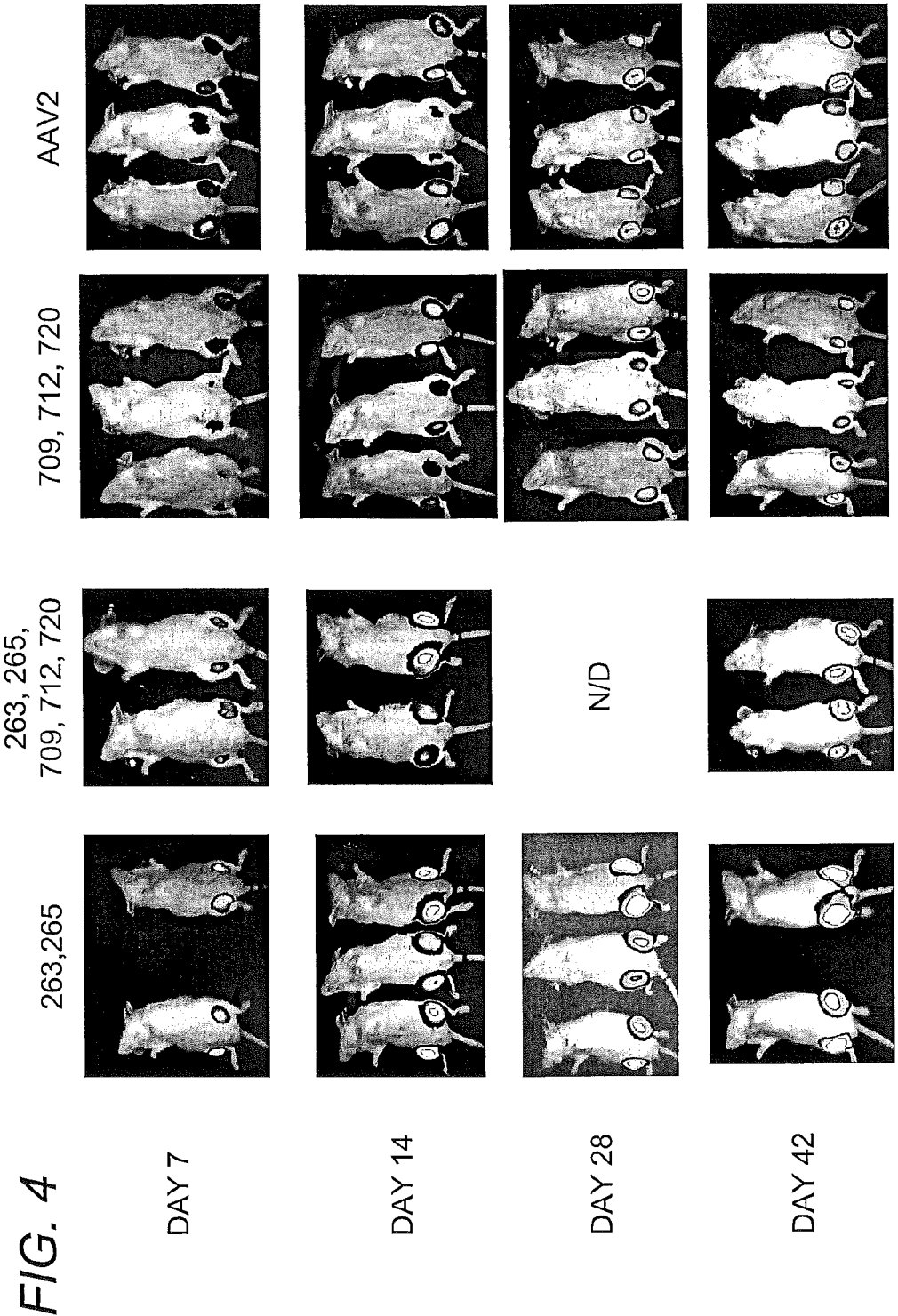

```
              1                                                    50
263,265   (1) MAADGYLPDWLEDTLSEGIRQWWKLKPGPPPPKPAERHKDDSRGLVLPGY
AAV2CAP   (1) MAADGYLPDWLEDTLSEGIRQWWKLKPGPPPPKPAERHKDDSRGLVLPGY 51                                                   100
263,265  (51) KYLGPFNGLDKGEPVNEADAAALEHDKAYDRQLDSGDNPYLKYNHADAEF
AAV2CAP  (51) KYLGPFNGLDKGEPVNEADAAALEHDKAYDRQLDSGDNPYLKYNHADAEF 101                                                  150
263,265 (101) QERLKEDTSFGGNLGRAVFQAKKRVLEPLGLVEEPVKTAPGKKRPVEHSP
AAV2CAP (101) QERLKEDTSFGGNLGRAVFQAKKRVLEPLGLVEEPVKTAPGKKRPVEHSP 151                                                  200
263,265 (151) VEPDSSSGTGKAGQQPARKRLNFGQTGDADSVPDPQPLGQPPAAPSGLGT
AAV2CAP (151) VEPDSSSGTGKAGQQPARKRLNFGQTGDADSVPDPQPLGQPPAAPSGLGT 201                                                  250
263,265 (201) NTMATGSGAPMADNNEGADGVGNSSGNWHCDSTWMGDRVITTSTRTWALP
AAV2CAP (201) NTMATGSGAPMADNNEGADGVGNSSGNWHCDSTWMGDRVITTSTRTWALP

251           * *                                    300
263,265 (251) TYNNHLYKQISSASTGASNDNHYFGYSTPWGYFDFNRFHCHFSPRDWQRL
AAV2CAP (251) TYNNHLYKQISSQS-GASNDNHYFGYSTPWGYFDFNRFHCHFSPRDWQRL 301                                                  350
263,265 (301) INNNWGFRPKRLNFKLFNIQVKEVTQNDGTTTIANNLTSTVQVFTDSEYQ
AAV2CAP (300) INNNWGFRPKRLNFKLFNIQVKEVTQNDGTTTIANNLTSTVQVFTDSEYQ 351                                                  400
263,265 (351) LPYVLGSAHQGCLPPFPADVFMVPQYGYLTLNNGSQAVGRSSFYCLEYFP
AAV2CAP (350) LPYVLGSAHQGCLPPFPADVFMVPQYGYLTLNNGSQAVGRSSFYCLEYFP 401                                                  450
263,265 (401) SQMLRTGNNFTFSYTFEDVPFHSSYAHSQSLDRLMNPLIDQYLYYLSRTN
AAV2CAP (400) SQMLRTGNNFTFSYTFEDVPFHSSYAHSQSLDRLMNPLIDQYLYYLSRTN 451                                                  500
263,265 (451) TPSGTTTQSRLQFSQAGASDIRDQSRNWLPGPCYRQQRVSKTSADNNNSE
AAV2CAP (450) TPSGTTTQSRLQFSQAGASDIRDQSRNWLPGPCYRQQRVSKTSADNNNSE 501                                                  550
263,265 (501) YSWTGATKYHLNGRDSLVNPGPAMASHKDDEEKFFPQSGVLIFGKQGSEK
AAV2CAP (500) YSWTGATKYHLNGRDSLVNPGPAMASHKDDEEKFFPQSGVLIFGKQGSEK 551                                                  600
263,265 (551) TNVDIEKVMITDEEEIRTTNPVATEQYGSVSTNLQRGNRQAATADVNTQG
AAV2CAP (550) TNVDIEKVMITDEEEIRTTNPVATEQYGSVSTNLQRGNRQAATADVNTQG 601                                                  650
263,265 (601) VLPGMVWQDRDVYLQGPIWAKIPHTDGHFHPSPLMGGFGLKHPPPQILIK
AAV2CAP (600) VLPGMVWQDRDVYLQGPIWAKIPHTDGHFHPSPLMGGFGLKHPPPQILIK 651                                                  700
263,265 (651) NTPVPANPSTTFSAAKFASFITQYSTGQVSVEIEWELQKENSKRWNPEIQ
AAV2CAP (650) NTPVPANPSTTFSAAKFASFITQYSTGQVSVEIEWELQKENSKRWNPEIQ 701                    736
263,265 (701) YTSNYNKSVNVDFTVDTNGVYSEPRPIGTRYLTRNL
AAV2CAP (700) YTSNYNKSVNVDFTVDTNGVYSEPRPIGTRYLTRNL
```

FIG. 9

```
                         1                                                50
AAV3bCAP      (1) MAADGYLPDWLEDNLSEGIREWWALKPGVPQPKANQQHQDNRRGLVLPGY
263,265       (1) MAADGYLPDWLEDNLSEGIREWWALKPGVPQPKANQQHQDNRRGLVLPGY 51                                               100
AAV3bCAP     (51) KYLGPGNGLDKGEPVNEADAAALEHDKAYDQQLKAGDNPYLKYNHADAEF
263,265      (51) KYLGPGNGLDKGEPVNEADAAALEHDKAYDQQLKAGDNPYLKYNHADAEF 101                                               150
AAV3bCAP    (101) QERLQEDTSFGGNLGRAVFQAKKRILEPLGLVEEAAKTAPGKKRPVDQSP
263,265     (101) QERLQEDTSFGGNLGRAVFQAKKRILEPLGLVEEAAKTAPGKKRPVDQSP 151                                               200
AAV3bCAP    (151) QEPDSSSGVGKSGKQPARKRLNFGQTGDSESVPDPQPLGEPPAAPTSLGS
263,265     (151) QEPDSSSGVGKSGKQPARKRLNFGQTGDSESVPDPQPLGEPPAAPTSLGS 201                                               250
AAV3bCAP    (201) NTMASGGGAPMADNNEGADGVGNSSGNWHCDSQWLGDRVITTSTRTWALP
263,265     (201) NTMASGGGAPMADNNEGADGVGNSSGNWHCDSQWLGDRVITTSTRTWALP

251            * *                                300
AAV3bCAP    (251) TYNNHLYKQISSQS-GASNDNHYFGYSTPWGYFDFNRFHCHFSPRDWQRL
263,265     (251) TYNNHLYKQISSASTGASNDNHYFGYSTPWGYFDFNRFHCHFSPRDWQRL 301                                               350
AAV3bCAP    (300) INNNWGFRPKKLSFKLFNIQVKEVTQNDGTTTIANNLTSTVQVFTDSEYQ
263,265     (301) INNNWGFRPKKLSFKLFNIQVKEVTQNDGTTTIANNLTSTVQVFTDSEYQ 351                                               400
AAV3bCAP    (350) LPYVLGSAHQGCLPPFPADVFMVPQYGYLTLNNGSQAVGRSSFYCLEYFP
263,265     (351) LPYVLGSAHQGCLPPFPADVFMVPQYGYLTLNNGSQAVGRSSFYCLEYFP 401                                               450
AAV3bCAP    (400) SQMLRTGNNFQFSYTFEDVPFHSSYAHSQSLDRLMNPLIDQYLYYLNRTQ
263,265     (401) SQMLRTGNNFQFSYTFEDVPFHSSYAHSQSLDRLMNPLIDQYLYYLNRTQ 451                                               500
AAV3bCAP    (450) GTTSGTTNQSRLLFSQAGPQSMSLQARNWLPGPCYRQQRLSKTANDNNNS
263,265     (451) GTTSGTTNQSRLLFSQAGPQSMSLQARNWLPGPCYRQQRLSKTANDNNNS 501                                               550
AAV3bCAP    (500) NFPWTAASKYHLNGRDSLVNPGPAMASHKDDEEKFFPMHGNLIFGKEGTT
263,265     (501) NFPWTAASKYHLNGRDSLVNPGPAMASHKDDEEKFFPMHGNLIFGKEGTT 551                                               600
AAV3bCAP    (550) ASNAELDNVMITDEEEIRTTNPVATEQYGTVANNLQSSNTAPTTRTVNDQ
263,265     (551) ASNAELDNVMITDEEEIRTTNPVATEQYGTVANNLQSSNTAPTTRTVNDQ 601                                               650
AAV3bCAP    (600) GALPGMVWQDRDVYLQGPIWAKIPHTDGHFHPSPLMGGFGLKHPPPQIMI
263,265     (601) GALPGMVWQDRDVYLQGPIWAKIPHTDGHFHPSPLMGGFGLKHPPPQIMI 651                                               700
AAV3bCAP    (650) KNTPVPANPPTTFSPAKFASFITQYSTGQVSVEIEWELQKENSKRWNPEI
263,265     (651) KNTPVPANPPTTFSPAKFASFITQYSTGQVSVEIEWELQKENSKRWNPEI 701                      737
AAV3bCAP    (700) QYTSNYNKSVNVDFTVDTNGVYSEPRPIGTRYLTRNL
263,265     (701) QYTSNYNKSVNVDFTVDTNGVYSEPRPIGTRYLTRNL
```

FIG. 10

```
             1                                                    50
2.5CAP    (1)MAADGYLPDWLEDTLSEGIRQWWKLKPGPPPPKPAERHKDDSRGLVLPGY
AAV2CAP   (1)MAADGYLPDWLEDTLSEGIRQWWKLKPGPPPPKPAERHKDDSRGLVLPGY 51                                                   100
2.5CAP   (51)KYLGPFNGLDKGEPVNEADAAALEHDKAYDRQLDSGDNPYLKYNHADAEF
AAV2CAP  (51)KYLGPFNGLDKGEPVNEADAAALEHDKAYDRQLDSGDNPYLKYNHADAEF 101                                                  150
2.5CAP  (101)QERLKEDTSFGGNLGRAVFQAKKRVLEPLGLVEEPVKTAPGKKRPVEHSP
AAV2CAP (101)QERLKEDTSFGGNLGRAVFQAKKRVLEPLGLVEEPVKTAPGKKRPVEHSP 151                                                  200
2.5CAP  (151)VEPDSSSGTGKAGQQPARKRLNFGQTGDADSVPDPQPLGQPPAAPSGLGT
AAV2CAP (151)VEPDSSSGTGKAGQQPARKRLNFGQTGDADSVPDPQPLGQPPAAPSGLGT 201                                                  250
2.5CAP  (201)NTMATGSGAPMADNNEGADGVGNSSGNWHCDSTWMGDRVITTSTRTWALP
AAV2CAP (201)NTMATGSGAPMADNNEGADGVGNSSGNWHCDSTWMGDRVITTSTRTWALP

251      * *                                         300
2.5CAP  (251)TYNNHLYKQISSASTGASNDNHYFGYSTPWGYFDFNRFHCHFSPRDWQRL
AAV2CAP (251)TYNNHLYKQISSQS-GASNDNHYFGYSTPWGYFDFNRFHCHFSPRDWQRL 301                                                  350
2.5CAP  (301)INNNWGFRPKRLNFKLFNIQVKEVTQNDGTTTIANNLTSTVQVFTDSEYQ
AAV2CAP (300)INNNWGFRPKRLNFKLFNIQVKEVTQNDGTTTIANNLTSTVQVFTDSEYQ 351                                                  400
2.5CAP  (351)LPYVLGSAHQGCLPPFPADVFMVPQYGYLTLNNGSQAVGRSSFYCLEYFP
AAV2CAP (350)LPYVLGSAHQGCLPPFPADVFMVPQYGYLTLNNGSQAVGRSSFYCLEYFP 401                                                  450
2.5CAP  (401)SQMLRTGNNFTFSYTFEDVPFHSSYAHSQSLDRLMNPLIDQYLYYLSRTN
AAV2CAP (400)SQMLRTGNNFTFSYTFEDVPFHSSYAHSQSLDRLMNPLIDQYLYYLSRTN 451                                                  500
2.5CAP  (451)TPSGTTTQSRLQFSQAGASDIRDQSRNWLPGPCYRQQRVSKTSADNNNSE
AAV2CAP (450)TPSGTTTQSRLQFSQAGASDIRDQSRNWLPGPCYRQQRVSKTSADNNNSE 501                                                  550
2.5CAP  (501)YSWTGATKYHLNGRDSLVNPGPAMASHKDDEEKFFPQSGVLIFGKQGSEK
AAV2CAP (500)YSWTGATKYHLNGRDSLVNPGPAMASHKDDEEKFFPQSGVLIFGKQGSEK 551                                                  600
2.5CAP  (551)TNVDIEKVMITDEEEIRTTNPVATEQYGSVSTNLQRGNRQAATADVNTQG
AAV2CAP (550)TNVDIEKVMITDEEEIRTTNPVATEQYGSVSTNLQRGNRQAATADVNTQG 601                                                  650
2.5CAP  (601)VLPGMVWQDRDVYLQGPIWAKIPHTDGHFHPSPLMGGFGLKHPPPQILIK
AAV2CAP (600)VLPGMVWQDRDVYLQGPIWAKIPHTDGHFHPSPLMGGFGLKHPPPQILIK 651                                                  700
2.5CAP  (651)NTPVPANPSTTFSAAKFASFITQYSTGQVSVEIEWELQKENSKRWNPEIQ
AAV2CAP (650)NTPVPANPSTTFSAAKFASFITQYSTGQVSVEIEWELQKENSKRWNPEIQ

701  *   *       *                     736
2.5CAP  (701)YTSNYAKSANVDFTVDNNGVYSEPRPIGTRYLTRNL
AAV2CAP (700)YTSNYNKSVNVDFTVDTNGVYSEPRPIGTRYLTRNL
```

FIG. 11

SEQUENCE LISTING

```
<160> NUMBER OF SEQ ID NOS: 16

<210> SEQ ID NO 1
<211> LENGTH: 736
<212> TYPE: PRT
<213> ORGANISM: adeno-associated virus 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
```

```
            35                  40                  45
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
                290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
                370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
450                 455                 460
```

-continued

```
Arg Gly Ser Pro Ala Gly Met Ser Val Gln Pro Lys Asn Trp Leu Pro
465                 470                 475                 480

Gly Pro Cys Tyr Arg Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
                515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 737
<212> TYPE: PRT
<213> ORGANISM: adeno-associated virus 7

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
```

```
                100             105             110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Ala Lys Lys Arg
            130                 135             140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
            165                 170                 175
Thr Gly Asp Ser Glu Ser Val Pro Asp Pro Gln Pro Leu Gly Glu Pro
            180                 185                 190
Pro Ala Ala Pro Ser Ser Val Gly Ser Gly Thr Val Ala Ala Gly Gly
            195                 200                 205
Gly Ala Pro Met Ala Asp Asn Asn Glu Gly Ala Asp Gly Val Gly Asn
            210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
            245                 250                 255
Leu Tyr Lys Gln Ile Ser Ser Glu Thr Ala Gly Ser Thr Asn Asp Asn
            260                 265                 270
Thr Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
            325                 330                 335
Asn Leu Thr Ser Thr Ile Gln Val Phe Ser Asp Ser Glu Tyr Gln Leu
            340                 345                 350
Pro Tyr Val Leu Gly Ser Ala His Gln Gly Cys Leu Pro Pro Phe Pro
            355                 360                 365
Ala Asp Val Phe Met Ile Pro Gln Tyr Gly Tyr Leu Thr Leu Asn Asn
            370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
            405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ala
            435                 440                 445
Arg Thr Gln Ser Asn Pro Gly Gly Thr Ala Gly Asn Arg Glu Leu Gln
            450                 455                 460
Phe Tyr Gln Gly Gly Pro Ser Thr Met Ala Glu Gln Ala Lys Asn Trp
465                 470                 475                 480
Leu Pro Gly Pro Cys Phe Arg Gln Gln Arg Val Ser Lys Thr Leu Asp
            485                 490                 495
Gln Asn Asn Asn Ser Asn Phe Ala Trp Thr Gly Ala Thr Lys Tyr His
            500                 505                 510
Leu Asn Gly Arg Asn Ser Leu Val Asn Pro Gly Val Ala Met Ala Thr
            515                 520                 525
```

-continued

```
His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Thr Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 3
<211> LENGTH: 735
<212> TYPE: PRT
<213> ORGANISM: adeno-associated virus 2

<400> SEQUENCE: 3

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160
```

```
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
```

```
Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 4
<211> LENGTH: 738
<212> TYPE: PRT
<213> ORGANISM: adeno-associated virus 8

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220
```

-continued

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ala Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
            405                 410                 415

Thr Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
        500                 505                 510

Leu Asn Gly Arg Asn Ser Leu Ala Asn Pro Gly Ile Ala Met Ala Thr
    515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Asn Thr Ala
        580                 585                 590

Pro Gln Ile Gly Thr Val Asn Ser Gln Gly Ala Leu Pro Gly Met Val
    595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640
```

```
Gly Leu Lys His Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
        660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 5
<211> LENGTH: 72
<212> TYPE: PRT
<213> ORGANISM: adeno-associated virus 1

<400> SEQUENCE: 5

Gly Ala Asp Gly Val Gly Asn Ala Ser Gly Asn Trp His Cys Asp Ser
1               5                   10                  15

Thr Trp Leu Gly Asp Arg Val Ile Thr Thr Ser Thr Arg Thr Trp Ala
            20                  25                  30

Leu Pro Thr Tyr Asn Asn His Leu Tyr Lys Gln Ile Ser Ser Ala Ser
        35                  40                  45

Thr Gly Ala Ser Asn Asp Asn His Tyr Phe Gly Tyr Ser Thr Pro Trp
    50                  55                  60

Gly Tyr Phe Asp Phe Asn Arg Phe
65                  70

<210> SEQ ID NO 6
<211> LENGTH: 71
<212> TYPE: PRT
<213> ORGANISM: adeno-associated virus 2

<400> SEQUENCE: 6

Gly Ala Asp Gly Val Gly Asn Ser Ser Gly Asn Trp His Cys Asp Ser
1               5                   10                  15

Thr Trp Met Gly Asp Arg Val Ile Thr Thr Ser Thr Arg Thr Trp Ala
            20                  25                  30

Leu Pro Thr Tyr Asn Asn His Leu Tyr Lys Gln Ile Ser Ser Gln Ser
        35                  40                  45

Gly Ala Ser Asn Asp Asn His Tyr Phe Gly Tyr Ser Thr Pro Trp Gly
    50                  55                  60

Tyr Phe Asp Phe Asn Arg Phe
65                  70

<210> SEQ ID NO 7
<211> LENGTH: 71
<212> TYPE: PRT
<213> ORGANISM: adeno-associated virus 3A

<400> SEQUENCE: 7

Gly Ala Asp Gly Val Gly Asn Ser Ser Gly Asn Trp His Cys Asp Ser
1               5                   10                  15

Gln Trp Leu Gly Asp Arg Val Ile Thr Thr Ser Thr Arg Thr Trp Ala
            20                  25                  30
```

Leu Pro Thr Tyr Asn Asn His Leu Tyr Lys Gln Ile Ser Ser Gln Ser
        35                  40                  45

Gly Ala Ser Asn Asp Asn His Tyr Phe Gly Tyr Ser Thr Pro Trp Gly
 50                  55                  60

Tyr Phe Asp Phe Asn Arg Phe
 65                  70

<210> SEQ ID NO 8
<211> LENGTH: 68
<212> TYPE: PRT
<213> ORGANISM: adeno-associated virus 4

<400> SEQUENCE: 8

Gly Ala Asp Gly Val Gly Asn Ala Ser Gly Asp Trp His Cys Asp Ser
 1               5                  10                  15

Thr Trp Ser Glu Gly His Val Thr Thr Thr Ser Thr Arg Thr Trp Val
            20                  25                  30

Leu Pro Thr Tyr Asn Asn His Leu Tyr Lys Arg Leu Gly Glu Ser Leu
        35                  40                  45

Gln Ser Asn Thr Tyr Asn Gly Phe Ser Thr Pro Trp Gly Tyr Phe Asp
 50                  55                  60

Phe Asn Arg Phe
 65

<210> SEQ ID NO 9
<211> LENGTH: 72
<212> TYPE: PRT
<213> ORGANISM: adeno-associated virus 5

<400> SEQUENCE: 9

Gly Ala Asp Gly Val Gly Asn Ala Ser Gly Asp Trp His Cys Asp Ser
 1               5                  10                  15

Thr Trp Met Gly Asp Arg Val Val Thr Lys Ser Thr Arg Thr Trp Val
            20                  25                  30

Leu Pro Ser Tyr Asn Asn His Gln Tyr Arg Glu Ile Lys Ser Gly Ser
        35                  40                  45

Val Asp Gly Ser Asn Ala Asn Ala Tyr Phe Gly Tyr Ser Thr Pro Trp
 50                  55                  60

Gly Tyr Phe Asp Phe Asn Arg Phe
 65                  70

<210> SEQ ID NO 10
<211> LENGTH: 72
<212> TYPE: PRT
<213> ORGANISM: adeno-associated virus 7

<400> SEQUENCE: 10

Gly Ala Asp Gly Val Gly Asn Ala Ser Gly Asn Trp His Cys Asp Ser
 1               5                  10                  15

Thr Trp Leu Gly Asp Arg Val Ile Thr Thr Ser Thr Arg Thr Trp Ala
            20                  25                  30

Leu Pro Thr Tyr Asn Asn His Leu Tyr Lys Gln Ile Ser Ser Glu Thr
        35                  40                  45

Ala Gly Ser Thr Asn Asp Asn Thr Tyr Phe Gly Tyr Ser Thr Pro Trp
 50                  55                  60

Gly Tyr Phe Asp Phe Asn Arg Phe
 65                  70

<210> SEQ ID NO 11
<211> LENGTH: 73
<212> TYPE: PRT
<213> ORGANISM: adeno-associated virus 8

<400> SEQUENCE: 11

Gly Ala Asp Gly Val Gly Ser Ser Gly Asn Trp His Cys Asp Ser
1               5                   10                  15

Thr Trp Leu Gly Asp Arg Val Ile Thr Thr Ser Thr Arg Thr Trp Ala
            20                  25                  30

Leu Pro Thr Tyr Asn Asn His Leu Tyr Lys Gln Ile Ser Asn Gly Thr
        35                  40                  45

Ser Gly Gly Ala Thr Asn Asp Asn Thr Tyr Phe Gly Tyr Ser Thr Pro
    50                  55                  60

Trp Gly Tyr Phe Asp Phe Asn Arg Phe
65                  70

<210> SEQ ID NO 12
<211> LENGTH: 73
<212> TYPE: PRT
<213> ORGANISM: adeno-associated virus 9

<400> SEQUENCE: 12

Gly Ala Asp Gly Val Gly Ser Ser Gly Asn Trp His Cys Asp Ser
1               5                   10                  15

Gln Trp Leu Gly Asp Arg Val Ile Thr Thr Ser Thr Arg Thr Trp Ala
            20                  25                  30

Leu Pro Thr Tyr Asn Asn His Leu Tyr Lys Gln Ile Ser Asn Ser Thr
        35                  40                  45

Ser Gly Gly Ser Ser Asn Asp Asn Ala Tyr Phe Gly Tyr Ser Thr Pro
    50                  55                  60

Trp Gly Tyr Phe Asp Phe Asn Arg Phe
65                  70

<210> SEQ ID NO 13
<211> LENGTH: 736
<212> TYPE: PRT
<213> ORGANISM: adeno-associated virus 2

<400> SEQUENCE: 13

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg

-continued

```
            130                 135                 140
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Val Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
        435                 440                 445

Thr Asn Thr Pro Ser Gly Thr Thr Thr Gln Ser Arg Leu Gln Phe Ser
        450                 455                 460

Gln Ala Gly Ala Ser Asp Ile Arg Asp Gln Ser Arg Asn Trp Leu Pro
465                 470                 475                 480

Gly Pro Cys Tyr Arg Gln Gln Arg Val Ser Lys Thr Ser Ala Asp Asn
                485                 490                 495

Asn Asn Ser Glu Tyr Ser Trp Thr Gly Ala Thr Lys Tyr His Leu Asn
                500                 505                 510

Gly Arg Asp Ser Leu Val Asn Pro Gly Pro Ala Met Ala Ser His Lys
        515                 520                 525

Asp Asp Glu Glu Lys Phe Phe Pro Gln Ser Gly Val Leu Ile Phe Gly
        530                 535                 540

Lys Gln Gly Ser Glu Lys Thr Asn Val Asp Ile Glu Lys Val Met Ile
545                 550                 555                 560
```

```
Thr Asp Glu Glu Glu Ile Arg Thr Thr Asn Pro Val Ala Thr Glu Gln
                565                 570                 575

Tyr Gly Ser Val Ser Thr Asn Leu Gln Arg Gly Asn Arg Gln Ala Ala
            580                 585                 590

Thr Ala Asp Val Asn Thr Gln Gly Val Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asn Pro Ser Thr Thr Phe Ser Ala Ala Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 14
<211> LENGTH: 737
<212> TYPE: PRT
<213> ORGANISM: adeno-associated virus 3B

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
```

```
            195                 200                 205
Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Lys Leu Ser Phe Lys Leu Phe Asn Ile Gln
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
                355                 360                 365

Asp Val Phe Met Val Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
                435                 440                 445

Thr Gln Gly Thr Thr Ser Gly Thr Thr Asn Gln Ser Arg Leu Leu Phe
450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
                595                 600                 605

Gln Asp Arg Asp Val Tyr Leu Gln Gly Pro Ile Trp Ala Lys Ile Pro
610                 615                 620
```

His Thr Asp Gly His Phe His Pro Ser Pro Leu Met Gly Gly Phe Gly
625                 630                 635                 640

Leu Lys His Pro Pro Gln Ile Met Ile Lys Asn Thr Pro Val Pro
            645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 15
<211> LENGTH: 736
<212> TYPE: PRT
<213> ORGANISM: adeno-associated virus 3B

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

-continued

```
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
            435                 440                 445
Gln Gly Thr Thr Ser Gly Thr Thr Asn Gln Ser Arg Leu Leu Phe Ser
450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
            515                 520                 525
Asp Asp Glu Glu Lys Phe Phe Pro Met His Gly Asn Leu Ile Phe Gly
530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Arg Thr Val Asn Asp Gln Gly Ala Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 16
<211> LENGTH: 736
<212> TYPE: PRT
<213> ORGANISM: adeno-associated virus 2

<400> SEQUENCE: 16

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320
```

-continued

```
Val Lys Glu Val Thr Gln Asn Asp Gly Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Val Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
            435                 440                 445

Thr Asn Thr Pro Ser Gly Thr Thr Thr Gln Ser Arg Leu Gln Phe Ser
            450                 455                 460

Gln Ala Gly Ala Ser Asp Ile Arg Asp Gln Ser Arg Asn Trp Leu Pro
465                 470                 475                 480

Gly Pro Cys Tyr Arg Gln Gln Arg Val Ser Lys Thr Ser Ala Asp Asn
            485                 490                 495

Asn Asn Ser Glu Tyr Ser Trp Thr Gly Ala Thr Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Gln Ser Gly Val Leu Ile Phe Gly
            530                 535                 540

Lys Gln Gly Ser Glu Lys Thr Asn Val Asp Ile Glu Lys Val Met Ile
545                 550                 555                 560

Thr Asp Glu Glu Glu Ile Arg Thr Thr Asn Pro Val Ala Thr Glu Gln
                565                 570                 575

Tyr Gly Ser Val Ser Thr Asn Leu Gln Arg Gly Asn Arg Gln Ala Ala
            580                 585                 590

Thr Ala Asp Val Asn Thr Gln Gly Val Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Ser Thr Thr Phe Ser Ala Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Ala Lys Ser Ala Asn Val Asp Phe Thr Val Asp Asn Asn Gly Val
705                 710                 715                 720

Tyr Ser Glu Pro Arg Pro Ile Gly Thr Arg Tyr Leu Thr Arg Asn Leu
                725                 730                 735
```

CHIMERIC VECTORS

CROSS-REFERENCE TO RELATED APPLICATIONS

This application is a continuation application of, and claims priority to U.S. patent application Ser. No. 11/793,430 filed Aug. 22, 2007, now U.S. Pat. No. 7,892,809, which is a 35 U.S.C. §371 national phase application of International Application No. PCT/US2005/045552, filed Dec. 15, 2005, which claims priority to U.S. Provisional Application No. 60/636,126, filed Dec. 15, 2004, the disclosures of each of which are incorporated herein by reference in their entireties.

STATEMENT OF GOVERNMENT SUPPORT

This invention was made with government support under Grant No. HL066973 awarded by the National Institutes of Health. The government has certain rights in the invention.

FIELD OF THE INVENTION

The present invention relates to novel chimeric viral vectors and methods of making and administering the same.

BACKGROUND OF THE INVENTION

It is becoming clear that vectors based upon adeno-associated virus (AAV) are the vectors of choice for certain gene therapy applications such as muscle delivery. The utilization of AAV vectors in such protocols is based on the advantageous properties of AAV. These properties include lack of pathogenicity and pathology, ease of preparation and purification, long term expression in many tissues including the muscle, and lack of a detrimental cell-mediated immune response.

AAV serotype 2 (AAV2) is the best studied of the AAV isolates. Over the past decade, inroads have been made in the evaluation of the tissue tropism of alternative AAV serotypes. These studies have shown that distinct AAV serotypes may be better suited for particular applications. In this regard, serotypes 1, 6 and 7 are the most promising for delivery to skeletal muscle. For example, as compared with AAV2, AAV1 can be administered at lower dosages (i.e., fewer particles) and can express the transgene at earlier time points and at higher levels of expression.

The purification schemes for AAV2 are well defined. Less streamlined are the purification parameters for some of the other AAV serotypes. It would be desirable to engineer a variant of AAV2 that exhibits advantageous properties, such as the enhanced muscle tropism of AAV1, 6 and 7, but still maintains its ease of purification. Increasing the range of available AAV vectors will also address additional concerns related to re-administration and immune responses.

Accordingly, it would be desirable to have available a broader array of AAV vectors.

SUMMARY OF THE INVENTION

The present invention provides chimeric virus vectors that have been designed to exhibit one or more properties of interest (e.g., enhanced tissue tropism). For example, the inventors have identified the key amino acid of AAV1 responsible for enhanced in vivo transduction and selectively engineered this amino acid into the backbone of AAV2 and AAV3b. In particular embodiments, the chimeric viruses of the invention have enhanced transduction capability (e.g., transduction of skeletal muscle, cardiac muscle, glial cells, astrocytes, liver, retina and/or lung, etc.), enhanced levels of transgene expression and/or earlier onset of transgene expression. The chimeric virus can also have a reduced transduction capability with respect to one or more cells or tissues (e.g., liver), which can be desirable in terms of targeting the vector to the target tissue of interest and reducing dosage of vector to be administered.

With respect to chimeric viruses based on AAV2 these chimeras can be designed to retain one or more of the desirable properties of this serotype (such as ease of purification and known safety), while exhibiting some of the advantageous properties of other AAV such as AAV1, AAV6 and/or AAV7 (including enhanced transduction of skeletal muscle), and/or other properties of interest that are not seen in other AAV or are present to a lesser extent in other AAV. Further, in particular embodiments, the chimeric virus has a different immunological profile than one or both of the parent viruses (i.e., is only weakly or not at all recognized by neutralizing antisera or antibodies against the parent virus), thereby allowing for administration to subjects that have antibodies directed against the parent virus or repeat administration following administration of another serotype.

Accordingly, as one aspect the invention provides a chimeric virus vector comprising:
(a) a chimeric AAV capsid comprising a selective amino acid insertion following amino acid position 264 in an AAV2 capsid subunit or a corresponding change in a capsid subunit from other AAV; and
(b) a nucleic acid comprising an AAV terminal repeat sequence and a heterologous nucleic acid sequence;
wherein the nucleic acid is packaged within the chimeric AAV capsid.

As another aspect, the invention also provides chimeric virus vector comprising:
(a) a chimeric AAV capsid comprising:
  (i) a selective amino acid substitution of an alanine for glutamine at amino acid position 263 in an AAV2 capsid subunit;
  (ii) a selective amino acid insertion of a threonine following amino acid position 264 in the AAV2 capsid subunit (e.g., immediately following amino acid position 264);
(b) a nucleic acid comprising an AAV terminal repeat sequence and a heterologous nucleic acid sequence;
wherein the nucleic acid is packaged within the chimeric AAV capsid.

The invention further provides a chimeric virus vector comprising:
(a) a chimeric AAV capsid comprising:
  (i) a selective amino acid substitution of an alanine for glutamine at amino acid position 263 in an AAV3b capsid subunit;
  (ii) a selective amino acid insertion of a threonine following amino acid position 264 in the AAV3b capsid subunit (e.g., immediately following amino acid position 264);
(b) a nucleic acid comprising an AAV terminal repeat sequence and a heterologous nucleic acid sequence;
wherein the nucleic acid is packaged within the chimeric AAV capsid.

As still another aspect, the invention provides chimeric virus vector comprising:
(a) a chimeric AAV capsid comprising a selective amino acid substitution at amino acid position 450 in an AAV2 capsid subunit or a corresponding change in a capsid subunit from other AAV;

(b) a nucleic acid comprising an AAV terminal repeat sequence and a heterologous nucleic acid sequence;
wherein the nucleic acid is packaged within the chimeric AAV capsid.

As yet another aspect, the invention provides a chimeric virus vector comprising:
(a) a chimeric AAV capsid comprising a selective amino acid substitution at amino acid position 457 in an AAV2 capsid subunit or a corresponding change in a capsid subunit from other AAV;
(b) a nucleic acid comprising an AAV terminal repeat sequence and a heterologous nucleic acid sequence;
wherein the nucleic acid is packaged within the chimeric AAV capsid.

Also provided are pharmaceutical formulations comprising the chimeric virus vectors of the invention.

The invention also provides methods of administering a nucleic acid to a cell comprising contacting the cell with a chimeric virus vector or pharmaceutical formulation of the invention.

As yet a further aspect, the invention provides methods of delivering a nucleic acid to a subject comprising administering to the subject a chimeric virus vector or pharmaceutical formulation of the invention.

The invention also provides for the use of the chimeric virus vectors of the invention in the manufacture of a medicament for the treatment of disease.

These and other aspects of the invention are set forth in more detail in the description of the invention below.

BRIEF DESCRIPTION OF THE DRAWINGS

FIGS. 1A-1B. Rationale of the triage approach. Four AAV serotypes (AAV1, AAV2, AAV7, and AAV8) were subjected to a multiple amino acid alignment using the Align program in the Vector NTI software suite. Amino acids similar in AAV1 (SEQ ID NO:1) and AAV7 (SEQ ID NO:2) and distinct from AAV2 (SEQ ID NO:3) and AAV8 (SEQ ID NO:4) or positions that contained amino acids that were different in the 4 serotypes were pinpointed as potential candidates. This led to the 36 potential candidates to engineer into AAV2. Elimination of amino acids that could not be modeled onto the crystal structure and molecular modeling of candidates onto the surface of the capsid led to the testing of the amino acids shown in FIG. 1C.

FIG. 1C. Alignment of AAV1 (SEQ ID NO:1) and AAV2 (SEQ ID NO:3) using the Align program in Vector NTI software package. The amino acids tested in the triage approach are shown with arrows. The circled amino acids correspond to those amino acids previously identified in Hauck et al., (2003) J. Virology 77:2768-2774).

FIG. 4. 263, 265 amino acids confer enhanced muscle tropism. Subsets (263, 265; 709, 712, 720) of the 2.5 variant were generated. $1 \times 10^{10}$ viral genome-containing particles were injected into each gastrocnemius of male Balb/c mice. Each mouse was imaged at 7, 14, 28, and 42 days post injection. The virus used in this experiment was purified using cesium chloride gradients. The 263, 265 variant exhibit enhanced muscle tropism similar to the 2.5 variant, whereas the 709, 712, 720 variant exhibited a muscle tropism profile similar to AAV2.

FIG. 9. Amino acid alignment of the capsid sequence of the 263, 265 mutant (SEQ ID NO:13) in an AAV2 background with the capsid sequence of AAV2 (SEQ ID NO:3). Amino acid 1 is numbered with respect to the VP1 sequence.

FIG. 10. Amino acid alignment of the capsid sequence of the 263, 265 mutant (SEQ ID NO:14) in an AAV3b background with the capsid sequence of AAV3b (SEQ ID NO:15). Amino acid 1 is numbered with respect to the VP1 sequence.

FIG. 11. Amino acid alignment of the capsid sequence of the 2.5 mutant (SEQ ID NO:16) in an AAV2 background with the capsid sequence of AAV2 (SEQ ID NO:3). Amino acid 1 is numbered with respect to the VP1 sequence.

DETAILED DESCRIPTION OF THE INVENTION

Figure 2A:
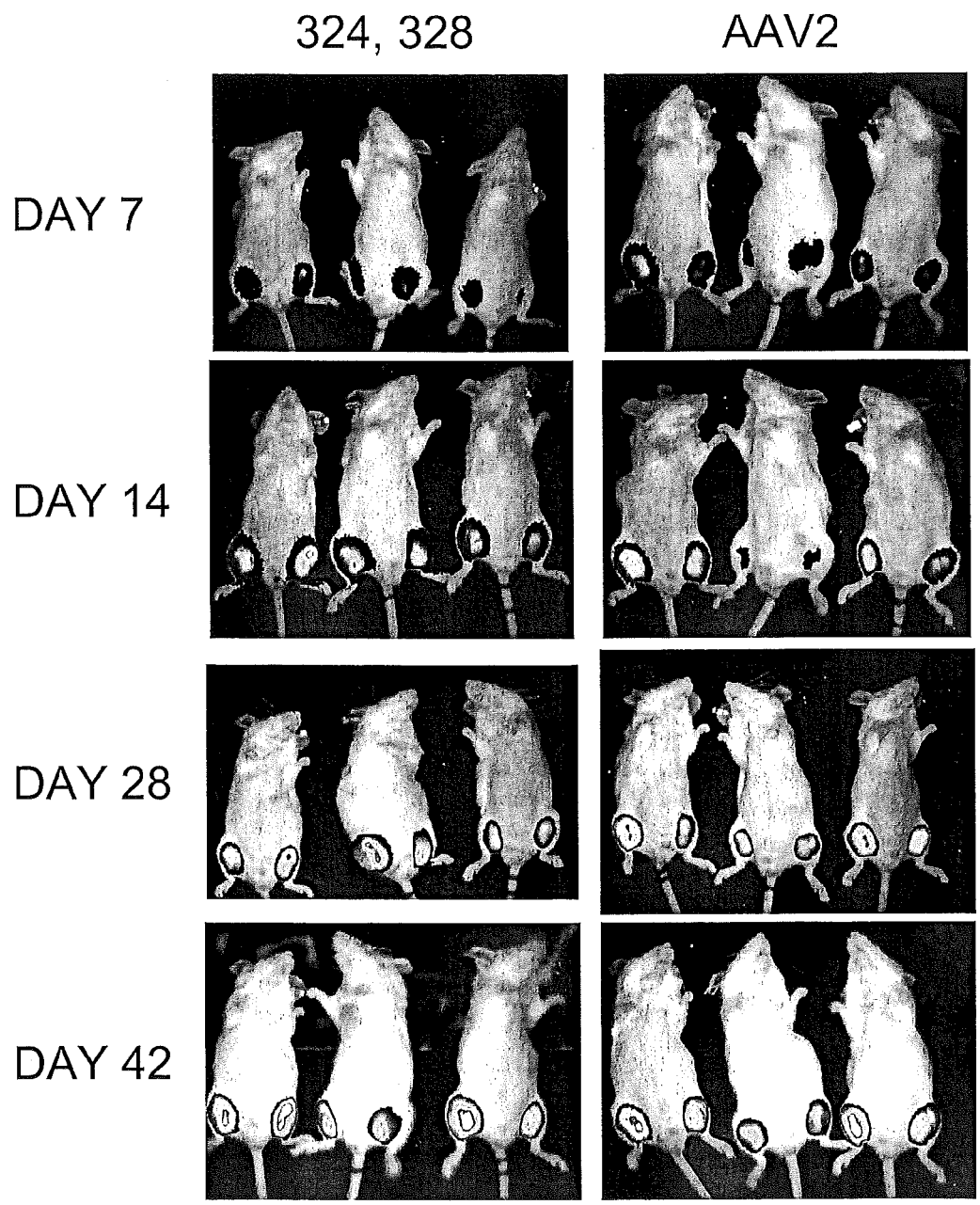
FIG. 2A. Changing the amino acid of AAV2 at the 324, 328 positions did not enhance muscle transduction. Amino acid positions 324, 328 of AAV2 were changed to that of AAV1. $1 \times 10^{10}$ viral genome-containing particles were injected into each gastrocnemius of male Balb/c mice. Each mouse was imaged at 7, 14, 28, and 42 days post injection. The virus used in this experiment was purified using cesium chloride gradients.

The present invention is based, in part, on the discovery that parvovirus (including AAV) capsids can be engineered to incorporate small, selective regions from other parvoviruses that confer desirable properties. The inventors have discovered that in some cases even a single amino acid insertion or substitution from a first parvovirus (e.g., an AAV) into the capsid structure of another parvovirus (e.g., an AAV) to create a chimeric parvovirus is sufficient to confer one or more of the desirable properties of the first parvovirus to the resulting chimeric parvovirus and/or to confer other properties that are not present in the first parvovirus or are present to a lesser extent.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The designation of all amino acid positions in the AAV capsid subunits in the description of the invention and the appended claims is with respect to VP1 capsid subunit numbering.

Except as otherwise indicated, standard methods known to those skilled in the art may be used for the construction of rAAV constructs, modified capsid proteins, packaging vectors expressing the parvovirus rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

Definitions.

The following terms are used in the description herein and the appended claims:

As used in the description of the invention and the appended claims, the singular forms "a," "an" and "the" are intended to include the plural forms as well, unless the context clearly indicates otherwise.

The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus*, and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, and B19 virus. Other autonomous parvoviruses are known to those skilled in the art. See, e.g., BERNARD N. FIELDS et al., VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV or any other AAV now known or later discovered. See, e.g., BERNARD N. FIELDS et al., VIROLOGY, volume 2, chapter 69 (4th ed., Lippincott-Raven Publishers). Recently, a number of new AAV serotypes and clades have been identified (see, e.g., Gao et al., (2004) *J. Virology* 78:6381-6388 and Table 1).

The genomic sequences of the various serotypes of AAV and the autonomous parvoviruses, as well as the sequences of the terminal repeats (TRs), Rep proteins, and capsid subunits are known in the art. Such sequences may be found in the literature or in public databases such as GenBank. See, e.g., GenBank Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) *J. Virology* 45:555; Chiorini et al., (1998) *J. Virology* 71:6823; Chiorini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci. USA* 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996) "Characterization of Adeno-associated virus (AAV) DNA replication and integration," Ph.D. Dissertation, University of Pittsburgh, Pittsburgh, Pa. (incorporated herein it its entirety).

TABLE 1

| Complete Genomes | GenBank Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |

TABLE 1-continued

| Complete Genomes | GenBank Accession Number |
|---|---|
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The term "tropism" as used herein refers to preferential entry of the virus into certain cell or tissue types or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of transacting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus nucleic acid may take within the cell.

As used herein, "transduction" of a cell by AAV or a chimeric virus particle means the transfer of genetic material into the cell by the incorporation of nucleic acid into the AAV or chimeric virus particle and subsequent transfer into the cell.

As used herein, a "recipient" virus or virus capsid is the parent virus or virus capsid into which the modification is introduced to produce the chimera. A "donor" virus or virus capsid as used herein is a parent virus or virus capsid from which the modification is taken and transferred into the recipient to produce the chimera.

Unless indicated otherwise, "enhanced transduction" or "enhanced tropism," or similar terms, by the chimeric virus vectors and capsids of the invention means that there is an increase in transduction or tropism as compared with the parent virus that acted as a recipient and into which the modification was introduced to produce the chimera and/or the chimeric virus vector or capsid exhibits "enhanced transduction" or "enhanced tropism," or similar terms, as compared with the donor parent virus, i.e., there is an increase in transduction or tropism as compared with the parent virus that acted as a donor and from which the modification was taken and introduced into the recipient to produce the chimera. In particular embodiments, the chimeric virus or capsid has enhanced tropism or transduction for muscle cells (including skeletal muscle, diaphragm muscle and/or cardiac muscle), liver, cells of the eye (including retina, retinal pigment epithelium and/or cornea), brain cells (including glial cells, astrocytes, neurons and/or oligodendricytes), lung, epithelium cells (including gut and/or respiratory epithelial cells), dendritic cells, pancreatic cells (including islet cells), bone cells (e.g., bone marrow stem cells), hematopoietic stem cells, spleen cells, keratinocytes, fibroblasts, endothelial cells, prostate cells, progenitor cells, or germ cells.

Similarly, unless indicated otherwise, by "reduced transduction" or "reduced tropism" or similar terms by the chimeric virus vectors and capsids of the invention, it is meant that there is a decrease in transduction or tropism as compared with the parent virus that acted as a recipient and into which the modification was introduced to produce the chimera and/or the chimeric virus vector or capsid exhibits "reduced transduction" or "reduced tropism," or similar terms, as compared with the donor parent virus, i.e., there is a decrease in transduction or tropism as compared with the parent virus that acted as a donor and from which the modification was taken and introduced into the recipient to produce the chimera. In particular embodiments, the chimeric virus or capsid has reduced tropism or transduction for muscle cells (including skeletal muscle, diaphragm muscle and/or cardiac muscle), liver, cells of the eye (including retina, retinal pigment epithelium and/or cornea), brain cells (including glial cells, astrocytes, neurons and/or oligodendricytes), lung, epithelium cells (including gut and/or respiratory epithelial cells), dendritic cells, pancreatic cells (including islet cells), bone cells (e.g., bone marrow stem cells), hematopoietic stem cells, spleen cells, keratinocytes, fibroblasts, endothelial cells, prostate cells, progenitor cells, or germ cells.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but are preferably either single or double stranded DNA sequences.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that can alleviate or reduce symptoms that result from an absence or defect in a protein in a cell or subject. Alternatively, a "therapeutic polypeptide" is a polypeptide that otherwise confers a benefit to a subject, e.g., anti-cancer effects or improvement in transplant survivability.

By the terms "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. Thus, the terms "treat," "treating" or "treatment of" (or grammatically equivalent terms) refer to both prophylactic and therapeutic regimens.

A "heterologous nucleotide sequence" or "heterologous nucleic acid" is typically a sequence that is not naturally occurring in the virus. Generally, the heterologous nucleic acid or nucleotide sequence comprises an open reading frame that encodes a polypeptide or nontranslated RNA.

As used herein, the term "vector" or "delivery vector" may refer to a parvovirus (e.g., AAV) particle that functions as a nucleic acid delivery vehicle, and which comprises viral DNA (i.e., the vector genome) packaged within a parvovirus (e.g., AAV) capsid. Alternatively, in some contexts, the term "vector" may be used to refer to the vector genome/vDNA in the absence of the capsid.

As used herein, a "recombinant parvovirus vector genome" is a parvovirus genome (i.e., vDNA) that comprises at least one terminal repeat (e.g., two terminal repeats) and one or more heterologous nucleotide sequences. A "recombinant parvovirus particle" comprises a recombinant parvovirus vector genome packaged within a parvovirus capsid.

A "rAAV vector genome" or "rAAV genome" is an AAV genome (i.e., vDNA) that comprises at least one terminal repeat (e.g., two terminal repeats) and one or more heterologous nucleotide sequences. rAAV vectors generally require only the 145 base terminal repeat(s) (TR(s)) in cis to generate virus. All other viral sequences are dispensable and may be supplied in trans (Muzyczka, (1992) *Curr. Topics Microbiol. Immunol.* 158:97). Typically, the rAAV vector genome will only retain the minimal TR sequence(s) so as to maximize the size of the transgene that can be efficiently packaged by the vector. The structural and non-structural protein coding sequences may be provided in trans (e.g., from a vector, such as a plasmid, or by stably integrating the sequences into a packaging cell). The rAAV vector genome optionally comprises two AAV TRs, which generally will be at the 5' and 3' ends of the heterologous nucleotide sequence(s), but need not be contiguous thereto. The TRs can be the same or different from each other.

A "rAAV particle" comprises a rAAV vector genome packaged within an AAV capsid.

A "parvovirus terminal repeat" may be from any parvovirus, including autonomous parvoviruses and AAV (all as defined above). An "AAV terminal repeat" may be from any AAV, e.g., serotypes 1, 2, 3, 4, 5, 6, 7, 8, 9, 10 and 11. The term "terminal repeat" includes synthetic sequences that function as an AAV inverted terminal repeat, such as the "double-D sequence" as described in U.S. Pat. No. 5,478,745 to Samulski et al., the disclosure of which is incorporated in its entirety herein by reference. The AAV terminal repeats need not have a wild-type terminal repeat sequence (e.g., a wild-type sequence may be altered by insertion, deletion, truncation or missense mutations), as long as the terminal repeat mediates the desired functions, e.g., replication, virus packaging, integration, and/or provirus rescue, and the like.

The capsid structure of autonomous parvoviruses and AAV are described in more detail in BERNARD N. FIELDS et al., VIROLOGY, volume 2, chapters 69 & 70 (4th ed., Lippincott-Raven Publishers).

The chimeric virus vector of the invention can further be a "targeted" virus vector (e.g., having a directed tropism) and/or a "hybrid" parvovirus (i.e., in which the rAAV genome and viral capsid are from different parvoviruses) as described in international patent publication WO 00/28004 and Chao et al., (2000) *Molecular Therapy* 2:619. In particular embodiments, the rAAV genome and virus capsid are from different AAV.

In particular embodiments, all of the subunits of the virus capsid are derived from the same AAV capsid protein backbone. In other embodiments, the virus capsid comprises capsid proteins that are derived from different AAV backbones.

The chimeric viruses of the invention can further be duplexed parvovirus particles as described in international patent publication WO 01/92551.

Accordingly, as used herein, the terms "chimeric parvovirus" and "chimeric AAV" encompass hybrid, targeted and duplexed virus particles, as well as other modified forms of parvoviruses and AAV.

Chimeric Virus Vectors.

Selected regions within the AAV capsid can confer desirable properties to other AAV including, but not limited to, enhanced transduction ability (e.g., enhanced transduction of skeletal muscle cells), higher expression of a transgene delivered by the recombinant genome and/or earlier onset of transgene expression. These selected regions can be transferred or "engineered" into other AAV capsids to confer the property(ies) of interest to the resulting chimeric particle. To illustrate, in the case of AAV2, the inventors have discovered that with a single amino acid insertion from AAV1, AAV2 can acquire the enhanced transduction capability of AAV1, while retaining the ease of purification (i.e., retains the ability to bind heparin) and the known safety features of AAV2. Further, in particular embodiments, the resulting chimeric virus has a different immunological profile than the parent virus (e.g., is weakly or not at all recognized by neutralizing antiserum to the parent virus), thereby allowing for repeat administration to subjects that have developed antibodies against the parent virus. For example, the chimeric 2.5 vector described herein is only weakly recognized by neutralizing antisera against AAV2.

In the present studies, the inventors have compared the linear amino acid sequences of two serotypes with high levels of skeletal muscle transduction (AAV1 and AAV7) with two that are less effective in transducing skeletal muscle (AAV2 and AAV8). Although these four serotypes overall exhibit a high degree of sequence similarity, there are regions of divergence and the characteristics of these four serotypes as delivery vectors are distinct. Using sequence analysis, a number of candidate amino acids in AAV1 and/or AAV7 were identified for incorporation into AAV2 to determine if they would confer the enhanced skeletal muscle transduction of AAV1/7 to AAV2. This initial pool of candidate positions was narrowed considerably based on analysis of the known crystal structure of AAV2, e.g., to identify amino acid positions that are located in regions that are likely to affect the biology of the virus. This smaller group of amino acids was then substituted and/or inserted into AAV2, either individually or in combination and several of the resulting mutants demonstrated the enhanced skeletal muscle transduction of AAV1. Corresponding modifications can readily be introduced into other AAV based on the present disclosure. A "corresponding" modification can be an insertion and/or a substitution and/or a deletion. For example, a modification that is an insertion in AAV2 may be a substitution mutation in another AAV. Further, in still other AAV, a deletion mutation may bring an amino acid into the desired position within the capsid subunits. "Corresponding" modifications in other AAV will be apparent to those skilled in the art.

According to the present invention, a "selective" amino acid change(s) is introduced into the virus capsid. This approach is in contrast to previous work with whole subunit or large domain swaps between AAV serotypes (see, e.g., international patent publication WO 00/28004 and Hauck et al., (2003) *J. Virology* 77:2768-2774). A "selective" amino acid change results in the insertion and/or substitution and/or deletion of less than about 20, 18, 15, 12, 10, 9, 8, 7, 6, 5, 4 or 3 contiguous amino acids. In particular embodiments, only two contiguous amino acids or even point mutations (i.e., one amino acid) are inserted and/or substituted into and/or deleted from the capsid subunits.

One or more selective amino acid changes can be introduced at different positions within the capsid subunits. For example, in particular embodiments, two, three, four, five, six, seven, eight, nine, ten or more selective amino acid changes can be introduced into the AAV capsid subunits.

It will be understood that the term "chimeric virus vector" or "chimeric capsid" excludes those virus vectors or capsids that have the indicated amino acids at the specified positions in their native state (e.g., in the recipient virus and/or in the wild-type virus).

The invention contemplates that the chimeric viruses of the invention can be produced by modifying the capsids of any AAV now known or later discovered. Further, the recipient parent AAV that is to be modified can be one of the characterized AAV, e.g., AAV2, AAV3a or 3b, AAV4, AAV5, AAV8, AAV9, AAV10 or AAV11 (see also Table 1). Alternatively, the recipient parent virus may already have modifications/alterations as compared with the naturally occurring viruses (i.e., is derived from a wild-type AAV, e.g., AAV2, AAV3a, AAV3b, AAV4, AAV5, AAV6, AAV7, AAV8, AAV9, AAV10 and/or AAV11 or any other AAV now known or later discovered). Such viruses are also within the scope of the present invention. For example, the recipient virus can be an AAV that is derived from AAV8, but has a heparan sulfate-binding domain (e.g., from the AAV2 capsid) incorporated therein or can be an AAV that is modified to contain a poly-His sequence to facilitate purification. As another illustrative example, the AAV can be derived from any of the known serotypes or clades, but have a peptide targeting sequence incorporated therein. As yet another possibility, the AAV capsid can comprise capsid subunits from different serotypes. Thus, in particular embodiments, the recipient virus comprises a capsid from an AAV serotype or clade that has been modified to comprise sequences that are not from that serotype or clade (e.g., are exogenous to the wild-type virus). Further, a donor parent AAV from a modification that is to be transferred into a recipient is taken can be one of the characterized AAV, e.g., AAV2, AAV3a or 3b, AAV4, AAV5, AAV8, AAV9, AAV10 or AAV11, but is not so limited.

In representative embodiments, the invention provides a chimeric virus vector comprising: (a) a chimeric AAV capsid comprising a selective amino acid insertion following any of amino acid position 260, 261, 262, 263, 264, 265, 266, 267 and/or 268 (e.g., following amino acid position 264) in one or more of the AAV2 capsid subunits (VP1 numbering) or a corresponding change in one or more capsid subunits from other AAV; and (b) a nucleic acid comprising an AAV terminal repeat sequence and a heterologous nucleic acid sequence; wherein the nucleic acid is packaged within the chimeric AAV capsid. In particular embodiments, the chimeric virus vector has enhanced transduction or tropism, an altered immunological profile, enhanced transgene expression and/or earlier onset of transgene expression as compared with the recipient parent rAAV vector and/or a donor parent rAAV vector. By "following amino acid position X" it is intended that the insertion immediately follows the indicated amino acid position (for example, "following amino acid position 264" indicates a point insertion at position 265 or a larger insertion, e.g., from positions 265 to 268, etc.) or is within two or three amino acids of the indicated amino acid position.

The designation of all amino acid positions in the description of the invention and the appended claims is with respect to VP1 numbering. It will be understood by those skilled in the art that the modifications described herein can result in modifications in all of the VP1, VP2 and VP3 capsid subunits. In particular embodiments, the modifications of the invention are found in one, two or three of the subunits of the AAV capsid.

Those skilled in the art will appreciate that for some AAV the corresponding modification will be an insertion and/or a substitution, depending on whether the corresponding amino acid positions are partially or completely present in the virus or, alternatively, are completely absent. Likewise, when modifying AAV other than AAV2, the specific amino acid position(s) may be different than the position in AAV2. The corresponding amino acid position(s) will be readily apparent to those skilled in the art using well-known sequence alignment techniques (see, e.g., FIG. 7).

In particular embodiments, the modifications described herein can be introduced into the capsid subunit(s) at the position that corresponds to the position of the amino acid(s) of interest in the AAV1, AAV6 and/or AAV7 capsid subunit(s) or any other AAV from which the modification is derived. Based on crystal structure analysis, it will be clear that in some instances the insertion/substitution can be moved 1, 2, 3, 4 or 5 or even more amino acids in either direction and still confer the desired characteristic. Because many of the modifications are made in loop structures, those skilled in the art will understand that the result of the modification can be driven more by physical presentation on the surface of the virion than the specific amino acid position.

Amino acids to be substituted and/or inserted according to the present invention can be any naturally occurring amino acids, modified forms thereof or synthetic amino acids.

In representative embodiments, the insertion and/or substitution and/or deletion in the capsid subunit(s) results in the insertion, substitution and/or repositioning of an amino acid that maintains the hydrophilic loop structure in that region and/or an amino acid that alters the configuration of the loop structure, a charged amino acid, or an amino acid that can be phosphorylated or sulfated or otherwise acquire a charge by post-translational modification (e.g., glycosylation) following any of amino acid position 260, 261, 262, 263, 264, 265, 266, 267 and/or 268 (e.g., following position 264) in an AAV2 capsid subunit(s) or a corresponding change in a capsid subunit(s) of another AAV. In particular embodiments, the chimeric virus vector has enhanced transduction for one or more cell types s compared with the recipient parent rAAV vector and/or a donor parent rAAV vector. Suitable amino acids include aspartic acid, glutamic acid, lysine, arginine, threonine, serine, tyrosine, glycine, alanine, proline, asparagine or glutamine. In particular embodiments, a threonine is inserted or substituted into the capsid subunit.

According to this aspect of the invention, in particular embodiments the chimeric virus vector comprises a chimeric AAV capsid comprising an amino acid insertion following amino acid position 264 in an AAV2, AAV3a or AAV3b capsid subunit(s) or in the corresponding position in an AAV2, AAV3a or AAV3b capsid that has been modified to comprise non-AAV2, AAV3a or AAV3b sequences, respectively (i.e., is derived from AAV2, AAV3a or AAV3b). The amino acid corresponding to position 264 in an AAV2 (or AAV3a or AAV3b) capsid subunit(s) will be readily identifiable in the starting virus that has been derived from AAV2 (or AAV3a or AAV3b), which can then be further modified according to the present invention.

In particular embodiments, the chimeric virus vectors can comprise a chimeric AAV2, AAV3a or AAV3b capsid comprising an amino acid insertion following amino acid position 264 in an AAV2, AAV3a or AAV3b capsid subunit(s). Suitable amino acid insertions are described above. Illustrative examples of corresponding mutations in other AAV are shown in Table 2 (Position 2). Amino acid substitutions and insertions are as described above. In particular embodiments, the insertion or substitution is a threonine (excepting AAV1, AAV6 and other AAV that have a threonine at this position).

TABLE 2

| Serotype | Position 1 | Position 2 |
| --- | --- | --- |
| AAV1 | A263X | T265X |
| AAV2 | Q263X | –265X |
| AAV3a | Q263X | –265X |
| AAV3b | Q263X | –265X |
| AAV4 | S257X | –259X |
| AAV5 | G253X | V255X |
| AAV6 | A263X | T265X |
| AAV7 | E264X | A266X |
| AAV8 | G264X | S266X |
| AAV9 | S263X | S265X |

Where, (X) → mutation to any amino acid (–) → insertion of any amino acid
Note:
Position 2 inserts are indicated by the site of insertion The invention further provides chimeric virus vectors comprising a chimeric AAV capsid comprising one or more selective amino acid insertions and/or substitutions selected from the group consisting of:
(a) a selective amino acid insertion following any of amino acid position 260, 261, 262, 263, 264, 265, 266, 267 and/or 268 (e.g., following amino acid position 264) in an AAV2 capsid subunit(s) or a corresponding change in a capsid subunit(s) from other AAV;
(b) a selective amino acid substitution at an amino acid from position 260 to 266 (e.g., position 263) in an AAV2 capsid subunit(s) or a corresponding change in a capsid subunit(s) from other AAV;
(c) a selective amino acid substitution at amino acid position 705 in an AAV2 capsid subunit(s) or a corresponding change in a capsid subunit(s) from other AAV;
(d) a selective amino acid substitution at amino acid position 708 in an AAV2 capsid subunit(s) or a corresponding change in a capsid subunit(s) from other AAV;
(e) a selective amino acid substitution at amino acid position 716 in an AAV2 capsid subunit(s) or a corresponding change in a capsid subunit(s) from other AAV;
(f) a selective amino acid substitution at an amino acid from position 447 to 453 (e.g., position 450) in an AAV2 capsid subunit(s) or a corresponding change in a capsid subunit(s) from other AAV; and
(g) a selective amino acid substitution at an amino acid from position 454 to 460 (e.g., position 457) in an AAV2 capsid subunit(s) or a corresponding change in a capsid subunit(s) from other AAV.

These modifications can be used alone or in any combination with each other and in any combination with any of the other modifications described herein.

In particular embodiments, the chimeric virus vector has enhanced transduction, enhanced transgene expression, earlier onset of transgene expression and/or an altered immunological profile as compared with the recipient parent rAAV vector and/or a donor parent rAAV vector.

In representative embodiments, the chimeric virus vector comprises a chimeric AAV2 capsid comprising an amino acid substitution at amino acid position 263 in an AAV2 capsid subunit(s) or in the corresponding position in an AAV2 capsid that has been modified to comprise non-AAV2 sequences. Alternatively, the chimeric virus vector can comprise a chimeric AAV3b capsid comprising an amino acid substitution at amino acid position 263 in an AAV3b capsid subunit(s) or in the corresponding position in an AAV3b capsid that has been modified to comprise non-AAV3b sequences.

Corresponding modifications can be made in other AAV. For example, in still other embodiments, the substitution is at amino acid position 263 of AAV1, a substitution at amino acid position 263 in AAV3a or AAV3b, or at the corresponding position(s) in an AAV capsid from any of the foregoing serotypes that has been modified to comprise exogenous sequences. Nonlimiting examples of corresponding mutations are shown in Table 2 (Position 1). Suitable amino acid substitutions are described below. In particular embodiments, an alanine is substituted into the capsid subunit(s) at the indicated position (excepting AAV1 and AAV6 and other AAV that have an alanine at this position).

Suitable amino acid substitutions include but are not limited to substitutions of small nonpolar amino acids such as alanine, glycine, valine, leucine or isoleucine or even proline, asparagine, serine or threonine into the capsid subunits (e.g., substitution of these amino acids for the glutamine found at position 263 in the AAV2, AAV3a or AAV3b capsid subunits). In particular embodiments, an alanine is substituted into the capsid subunit(s).

Another chimeric virus vector of the invention comprises a chimeric AAV2 capsid comprising an amino acid substitution at amino acid position 705 in an AAV2 capsid subunit(s) or at the corresponding position in an AAV2 capsid subunit that has been modified to comprise non-AAV2 sequences.

Corresponding changes can be made in other AAV. For example, in other embodiments, the invention provides for a chimeric virus vector having an amino acid substitution at amino acid position 706 of an AAV1 capsid subunit(s), a substitution at amino acid position 706 of an AAV3a capsid subunit(s), a substitution at amino acid position 706 of an AAV3b capsid subunit(s), a substitution at amino acid position 707 of an AAV7 capsid subunit(s), a substitution at amino acid position 708 of an AAV8 capsid subunit(s), or a substitution at amino acid position 706 of an AAV9 capsid subunit(s); or at the corresponding position(s) in an AAV capsid from any of the foregoing serotypes that has been modified to comprise exogenous sequences or at the corresponding position(s) of any other AAV.

In representative embodiments of the invention described in the previous two paragraphs, suitable amino acid substitutions include but are not limited to substitutions of serine, threonine, tyrosine, proline, glutamine, alanine, glycine, valine, leucine or isoleucine (e.g., substituted for the asparagine at this position in an AAV2 capsid subunit(s)). In particular embodiments, alanine is substituted into the capsid subunit(s).

A further chimeric virus vector according to the invention comprises a chimeric AAV2 capsid comprising an amino acid substitution at amino acid position 708 in an AAV2 capsid subunit(s) or at the corresponding position in an AAV2 capsid subunit(s) that has been modified to comprise non-AAV2 sequences.

Corresponding modifications can be made in other AAV. In some embodiments, the invention provides for a chimeric virus vector having an amino acid substitution at amino acid position 709 of an AAV1 capsid subunit(s), an amino acid substitution at amino acid position 709 of an AAV3a capsid subunit(s), an amino acid substitution at amino acid position 709 of an AAV3b capsid subunit(s), an amino acid substitution at amino acid position 710 of an AAV7 capsid subunit(s), an amino acid substitution at amino acid position 711 of an AAV8 capsid subunit(s), or an amino acid substitution at amino acid position 709 of an AAV9 capsid subunit(s); or at the corresponding position in an AAV capsid subunit(s) from any of the foregoing AAV that has been modified to comprise exogenous sequences or at a corresponding position in any other AAV.

In representative embodiments of the invention described in the previous two paragraphs, the substitution results in a substitution of serine, threonine, tyrosine, proline, asparagine, glutamine, alanine, glycine, leucine or isoleucine into the capsid subunit(s) (e.g., for the valine at this position in an AAV2 capsid subunit(s)). One exemplary substitution is a substitution of alanine into the capsid subunit(s).

The invention also provides a chimeric virus vector comprising a chimeric AAV2 capsid comprising an amino acid substitution at amino acid position 716 in an AAV2 capsid subunit(s) or at the corresponding position in an AAV2 capsid that has been modified to comprise non-AAV2 sequences.

Corresponding modifications can be made in other AAV. In particular embodiments, the invention provides for a chimeric virus vector having an amino acid substitution at amino acid position 717 of an AAV1 capsid subunit(s), an amino acid substitution at amino acid position 717 of an AAV3a capsid subunit(s), an amino acid substitution at amino acid position 717 of an AAV3b capsid subunit(s), an amino acid substitution at amino acid position 718 of an AAV7 capsid subunit(s), an amino acid substitution at amino acid position 719 of an AAV8 capsid subunit(s), or an amino acid substitution at amino acid position 717 of an AAV9 capsid subunit(s); or at the corresponding position in an AAV capsid subunit(s) from any of the foregoing AAV that has been modified to comprise exogenous sequences or at the corresponding position in any other AAV.

In particular aspects of the embodiments described in the previous two paragraphs, the substitution is a substitution of an amino acid that cannot be phosphorylated for an amino acid that can be phosphorylated (e.g., threonine). Alternatively, the substitution can be a substitution of a serine, tyrosine, glycine, alanine, proline, valine, leucine, isoleucine, asparagine or glutamine into the capsid subunit (e.g., substitution of the threonine at this position in AAV2). One particular chimeric virus comprises an asparagine substituted at this position into the capsid subunit(s).

A further chimeric virus vector according to the invention is a chimeric virus vector comprising a chimeric AAV2 capsid comprising an amino acid substitution at any of amino acid positions 447, 448, 449, 450, 451, 452 and/or 453 (e.g., at position 450) in an AAV2 capsid subunit(s) or at the corresponding position in an AAV2 capsid subunit(s) that has been modified to comprise non-AAV2 sequences or at the corresponding position of any other AAV. In particular embodiments, the substitution is a substitution of an amino acid that cannot be phosphorylated for an amino acid that can be phosphorylated (e.g., threonine). Alternatively, the substitution can be a substitution of a serine, tyrosine, glycine, alanine, proline, valine, leucine, isoleucine, asparagine or glutamine into the capsid subunit (e.g., substitution of the threonine at position 450 in AAV2). One particular chimeric virus comprises an asparagine substituted at this position into the capsid subunits.

Also provided is a chimeric virus vector comprising a chimeric AAV2 capsid comprising an amino acid substitution at any of amino acid position 454, 455, 456, 457, 458, 459 and/or 460 (e.g., at position 457) in an AAV2 capsid subunit(s) or at the corresponding position in an AAV2 capsid subunit(s) that has been modified to comprise non-AAV2 sequences or at the corresponding position of any other AAV. Suitable amino acid substitutions include substitution of a glycine, alanine, valine, lysine, isoleucine, proline, serine, threonine or asparagine into the capsid subunit(s). In representative embodiments, an asparagine is substituted into the capsid subunit (e.g., an asparagine is substituted for the glutamine found at position 457 in the AAV2 capsid subunits).

One non-limiting example of a chimeric virus vector of the invention comprises: (a) a chimeric AAV capsid (e.g., AAV2 capsid) comprising: (i) a selective amino acid insertion following amino acid position 264 in an AAV2 capsid subunit(s) or a corresponding change in a capsid subunit(s) from other AAV; and (ii) a selective amino acid substitution at amino acid position 263 in the AAV2 capsid subunit(s) or a corresponding change in the capsid subunit(s) from other AAV; and (b) a nucleic acid comprising an AAV TR sequence and a heterologous nucleic acid sequence; wherein the nucleic acid is packaged within the chimeric AAV capsid. In particular embodiments, the chimeric virus has enhanced transduction, enhanced transgene expression, earlier transgene expression and/or an altered immunological profile as compared with the recipient parent rAAV vector and/or a donor parent rAAV vector. For example, the chimeric virus vector can comprise a chimeric AAV2, AAV3a or AAV3b capsid in which a threonine has been inserted following amino acid position 264 in an AAV2 or AAV3b capsid subunit(s) and an alanine has been substituted for glutamine at amino acid position 263 in the AAV2, AAV3a or AAV3b capsid subunit(s); or these changes can be made at the corresponding positions in an AAV2, AAV3a or AAV3b capsid that has been modified to comprise non-AAV2, non-AAV3a or non-AAV3b sequences, respectively, or in the corresponding positions in any other AAV. The sequence of the 263, 265 variant described herein is shown in AAV2 (FIG. 9) and AAV3b (FIG. 10) backgrounds and compared with the sequence of the recipient parent virus.

Another exemplary chimeric virus vector of the invention comprises (a) a chimeric AAV capsid e.g., (AAV2 capsid) comprising: (i) a selective amino acid insertion following amino acid position 264 in an AAV2 capsid subunit(s) or a corresponding change in a capsid subunit(s) from other AAV; and (ii) a selective amino acid substitution at amino acid position 263 in the AAV2 capsid subunit(s) or a corresponding change in the capsid subunit(s) from other AAV; (iii) a selective amino acid substitution at amino acid position 705 in the AAV2 capsid subunit(s) or a corresponding change in the capsid subunit(s) from other AAV; (iv) a selective amino acid substitution at amino acid position 708 in the AAV2 capsid subunit(s) or a corresponding change in the capsid subunit(s) from other AAV; and (v) a selective amino acid substitution at amino acid position 7.16 in the AAV2 capsid subunit(s) or a corresponding change in the capsid subunit(s) from other AAV; and (b) a nucleic acid comprising an AAV TR sequence and a heterologous nucleic acid sequence; wherein the nucleic acid is packaged within the chimeric AAV capsid. In particular embodiments, the chimeric virus has enhanced transduction, enhanced transgene expression, earlier transgene expression and/or an altered immunological profile as compared with the recipient rAAV vector and/or a donor parent rAAV vector.

According to this embodiment, the chimeric virus vector can comprise a chimeric AAV capsid (e.g., AAV2 capsid) comprising:
    (a) a threonine insertion following amino acid position 264 in an AAV2 capsid subunit(s);
    (b) an alanine for glutamine substitution at amino acid position 263 in the AAV2 capsid subunit(s);
    (c) an alanine for asparagine substitution at amino acid position 705 in the AAV2 capsid subunit(s);
    (d) an alanine for valine substitution at amino acid position 708 in the AAV2 capsid subunit(s); and
    (e) an asparagine for threonine substitution at amino acid position 716 in the AAV2 capsid subunit(s);
    or these changes can be made at the corresponding positions in an AAV2 capsid that has been modified to comprise non-AAV2 sequences or at the corresponding positions in other AAV.

In particular embodiments, the chimeric virus vector can be the chimeric 2.5 variant disclosed herein. The sequence of the 2.5 mutant as compared with AAV2 is shown in FIG. 11.

The invention further provides a chimeric virus vector comprising:
    (a) a chimeric AAV capsid (e.g., AAV2 capsid) comprising:
        (i) a selective amino acid substitution at amino acid position 450 in an AAV2 capsid subunit(s) or a corresponding change in a capsid subunit(s) of other AAV; and
        (ii) a selective amino acid substitution at amino acid position 457 in the AAV2 capsid subunit(s) or a corresponding change in a capsid subunit(s) of other AAV; and
    (b) a nucleic acid comprising an AAV TR sequence and a heterologous nucleic acid sequence; wherein the nucleic acid is packaged within the chimeric AAV capsid.

In particular embodiments, the chimeric viral vector has enhanced transduction, enhanced transgene expression, earlier transgene expression and/or an altered immunological profile as compared with the recipient parent virus vector and/or a donor parent rAAV vector.

According to particular embodiments, a chimeric AAV2 capsid comprises (i) an asparagine for threonine substitution at amino acid position 450 in an AAV2 capsid subunit(s); and (ii) an asparagine for glutamine substitution at amino acid position 457 in the AAV2 capsid subunit(s); or these changes can be made at the corresponding positions in an AAV2 capsid subunit(s) that has been modified to comprise non-AAV2 sequences or at the corresponding positions of any other AAV.

Another exemplary chimeric virus vector of the invention comprises:
  (a) a chimeric AAV capsid (e.g., AAV2 capsid) comprising:
    (i) a selective amino acid insertion following amino acid position 264 in an AAV2 capsid subunit(s) or a corresponding change in a capsid subunit(s) of other AAV;
    (ii) a selective amino acid substitution at amino acid position 450 in the AAV2 capsid subunit(s) or a corresponding change in a capsid subunit(s) of other AAV; and
    (iii) a selective amino acid substitution at amino acid position 457 in the AAV2 capsid subunit(s) or a corresponding change in a capsid subunit(s) of other AAV; and
  (b) a nucleic acid comprising an AAV TR sequence and a heterologous nucleic acid sequence; wherein the nucleic acid is packaged within the chimeric AAV capsid.

In particular embodiments, the chimeric viral vector has enhanced transduction, enhanced transgene expression, earlier transgene expression and/or an altered immunological profile as compared with the recipient parent virus vector and/or a donor parent rAAV vector.

According to particular aspects of this embodiment of the invention, the chimeric virus vector comprises a chimeric AAV2 capsid comprising:
  (a) a threonine insertion following amino acid position 264 in the AAV2 capsid subunit(s);
  (b) an asparagine for threonine substitution at amino acid position 450 in the AAV2 capsid subunit(s); and
  (c) an asparagine for glutamine substitution at amino acid position 457 in the AAV2 capsid subunit(s);
  or these changes can be made at the corresponding positions in an AAV2 capsid that has been modified to comprise non-AAV2 sequences or at the corresponding positions of any other AAV.

The chimeric virus vectors of the invention generally comprise a rAAV vector genome, i.e., the AAV vector genome comprises one or more heterologous nucleic acids that encode a polypeptide or a non-translated RNA. Heterologous nucleic acids are discussed in more detail hereinbelow.

Chimeric Capsids.

The present invention further encompasses chimeric virus capsids essentially as described above, i.e., in the absence of a rAAV vector genome.

The chimeric virus capsids can be used as "capsid vehicles," as has been described in U.S. Pat. No. 5,863,541 (the disclosure of which is incorporated by reference herein in its entirety). Molecules that can be packaged by the chimeric virus capsids and transferred into a cell include heterologous DNA, RNA, polypeptides, small organic molecules, or combinations of the same. Heterologous molecules are defined as those that are not naturally found in an AAV infection, i.e., those not encoded by a wild-type AAV genome. Further, therapeutically useful molecules can be associated with the outside of the chimeric virus capsid for transfer of the molecules into host target cells. Such associated molecules can include DNA, RNA, small organic molecules, carbohydrates, lipids and/or polypeptides. In one embodiment of the invention the therapeutically useful molecule is covalently linked (i.e., conjugated or chemically coupled) to the capsid proteins. Methods of covalently linking molecules are known by those skilled in the art.

The chimeric virus capsids of the invention also find use in raising antibodies against the novel capsid structures. As a further alternative, an exogenous amino acid sequence may be inserted into the parvovirus capsid for antigen presentation to a cell, e.g., for administration to a subject to produce an immune response to the exogenous amino acid sequence.

According to some embodiments, chimeric virus capsids can be administered to a subject concurrently (e.g., within minutes or hours of each other) with an AAV vector or chimeric virus vector according to the invention. Further, the invention provides compositions and pharmaceutical formulations comprising the inventive chimeric virus capsids and an AAV vector or chimeric virus vector of the invention.

The invention also provides nucleic acids (optionally, isolated nucleic acids) encoding the chimeric virus capsids and capsid subunits of the invention. Further provided are vectors comprising the nucleic acids, and cells (in vivo or in culture) comprising the nucleic acids and/or vectors of the invention. Such nucleic acids, vectors and cells can be used, for example, as reagents (e.g., helper packaging constructs or packaging cells) for the production of chimeric virus capsids or vectors as described herein.

Methods of Producing Chimeric Virus Vectors.

The present invention further provides methods of producing the inventive chimeric virus vector.

In one particular embodiment, the present invention provides a method of producing a recombinant chimeric virus vector, comprising providing to a cell, (a) a rAAV template comprising (i) one or more heterologous nucleotide sequences, and (ii) packaging signal sequences sufficient for the encapsidation of the AAV template into chimeric virus particles, and (b) AAV sequences sufficient for replication and encapsidation of the rAAV template into chimeric viral particles (e.g., the AAV rep and chimeric cap sequences comprising one or more selective insertions, deletions and/or substitutions from other AAV therein). The rAAV template and AAV replication and capsid sequences are provided under conditions such that recombinant chimeric virus particles comprising the rAAV template packed within the chimeric capsid are produced in the cell. The method can further comprise the step of collecting the virus particles from the cell. Virus particles may be collected from the medium and/or by lysing the cells.

The cell is typically a cell that is permissive for AAV viral replication. Any suitable cell known in the art may be employed. Mammalian cells are preferred. Also preferred are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably carried (episomal or integrated) within a cell.

Typically, and preferably, the AAV rep/cap sequences will not be flanked by the AAV packaging sequences (e.g., AAV ITRs), to prevent rescue and/or packaging of these sequences.

The rAAV template can be provided to the cell using any method known in the art. For example, the rAAV template may be supplied by a non-viral (e.g., plasmid) or viral vector. In particular embodiments, the rAAV template is supplied by a herpesvirus or adenovirus vector (e.g., inserted into the E1a or E3 regions of a deleted adenovirus). As another illustration, Palombo et al., (1998) *J. Virology* 72:5025, describe a baculovirus vector carrying a reporter gene flanked by the AAV ITRs. EBV vectors may also be employed to deliver the rAAV template, as described above with respect to the rep/cap genes.

In another representative embodiment, the rAAV template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. It is preferred that these helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is preferably a hybrid adenovirus or hybrid herpesvirus comprising the AAV rep/cap genes.

In one particular preferred embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, it is preferred that the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV Rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Preferably, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of chimeric virus particles. Preferably, the virus stock has a titer of at least about $10^5$ transducing units (tu)/ml, more preferably at least about $10^6$ to/ml, more preferably at least about $10^7$ tu/ml, yet more preferably at least about $10^8$ to/ml, yet more preferably at least about $10^9$ to/ml, still yet more preferably at least about $10^{10}$ tu/ml.

Recombinant Parvovirus Vectors.

The parvovirus vectors of the present invention are useful for the delivery of nucleic acids to cells in vitro, ex vivo, and in vivo. In particular, the parvovirus vectors can be advantageously employed to deliver or transfer nucleic acids to animal, more preferably mammalian, cells.

Any heterologous nucleotide sequence(s) (as defined above) may be delivered in the chimeric virus vectors of the present invention. Nucleic acids of interest include nucleic acids encoding polypeptides, preferably therapeutic (e.g., for medical or veterinary uses) or immunogenic (e.g., for vaccines) polypeptides.

Therapeutic polypeptides include, but are not limited to, cystic fibrosis transmembrane regulator protein (CFTR), dystrophin (including the protein product of dystrophin minigenes, see, e.g, Vincent et al., (1993) *Nature Genetics* 5:130; U.S. Patent Publication No. 2003017131, the disclosures of which are incorporated herein in their entireties by reference), utrophin (Tinsley et al., (1996) *Nature* 384:349), clotting factors (e.g., Factor VIII, Factor IX, Factor X, etc.), erythropoietin, angiostatin, endostatin, catalase, tyrosine hydroxylase, superoxide dismutase, leptin, the LDL receptor, neprilysin, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukins-1 through -14, granulocyte-macrophage colony stimulating factor, lymphotoxin, and the like), peptide growth factors, neurotrophic factors and hormones (e.g., somatotropin, insulin, insulin-like growth factors including IGF-1 and IGF-2, platelet derived growth factor, epidermal growth factor, fibroblast growth factor, nerve growth factor, neurotrophic factor-3 and -4, brain-derived neurotrophic factor, glial derived growth factor, transforming growth factor-α and -β, and the like), bone morphogenic proteins (including RANKL and VEGF), lysosomal proteins, anti-apoptotic gene products, glutamate receptors, lymphokines, soluble CD4, Fc receptors, T cell receptors, ApoE, ApoC, protein phosphatase inhibitor 1 (I-1), phospholamban, serca2a, lysosomal acid α-glucosidase, α-galactosidase A, barkct, β2-adrenergic receptor, β2-adrenergic receptor kinase (BARK), phosphoinositide-3 kinase (PI3 kinase), calsarcin, a sarcoglycan (e.g., α, β, γ), receptors (e.g., the tumor necrosis growth factor-α soluble receptor), anti-inflammatory factors such as IRAP, monoclonal antibodies (including single chain monoclonal antibodies; an exemplary Mab is the herceptin Mab). Other illustrative heterologous nucleotide sequences encode suicide gene products (e.g., thymidine kinase, cytosine deaminase, diphtheria toxin, and tumor necrosis factors such as TNF-α), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof.

Heterologous nucleotide sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. No. 6,013,487; U.S. Pat. No. 6,083,702), interfering RNAs (RNAi) including small interfering RNAs (siRNA) that mediate gene silencing (see, Sharp et al., (2000) *Science* 287:2431) or other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against the multiple drug resistance (MDR) gene product (e.g., to treat tumors and/or for administration to the heart to prevent damage by chemotherapy), RNAi against myostatin (Duchenne muscular dystrophy), to treat or RNAi against VEGF (e.g., to treat tumors).

The parvovirus vector may also comprise a heterologous nucleotide sequence that shares homology with and recombines with a locus on the host chromosome. This approach may be utilized to correct a genetic defect in the host cell.

The present invention also provides parvovirus vectors that express an immunogenic polypeptide, e.g., for vaccination. The nucleic acid may encode any immunogen of interest known in the art including, but are not limited to, immunogens from human immunodeficiency virus, influenza virus, gag proteins, tumor antigens, cancer antigens, bacterial antigens, viral antigens, and the like.

The use of parvoviruses as vaccines is known in the art (see, e.g., Miyamura et al., (1994) *Proc. Nat. Acad. Sci USA* 91:8507; U.S. Pat. No. 5,916,563 to Young et al. U.S. Pat. No. 5,905,040 to Mazzara et al., U.S. Pat. No. 5,882,652, U.S. Pat. No. 5,863,541 to Samulski et al.; the disclosures of which are incorporated herein in their entireties by reference). The antigen may be presented in the parvovirus capsid. Alternatively, the antigen may be expressed from a heterologous nucleic acid introduced into a recombinant vector genome.

An immunogenic polypeptide, or immunogen, may be any polypeptide suitable for protecting the subject against a disease, including but not limited to microbial, bacterial, protozoal, parasitic, fungal and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio immunogen, herpes immunogen (e.g., CMV, EBV, HSV immunogens) mumps immunogen, measles immunogen, rubella immunogen, diphtheria toxin or other diptheria immunogen, pertussis antigen, hepatitis (e.g., hepatitis A, hepatitis B or hepatitis C) immunogen, or any other vaccine immunogen known in the art.

Alternatively, the immunogen may be any tumor or cancer cell antigen. Preferably, the tumor or cancer antigen is expressed on the surface of the cancer cell. Exemplary cancer and tumor cell antigens are described in S. A. Rosenberg, (1999) *Immunity* 10:281). Other illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124) including MART-1 (Coulie et al., (1991) *J. Exp. Med.* 180:35), gp100 (Wick et al., (1988) *J. Cutan. Pathol.* 4:201) and MAGE antigen, MAGE-1, MAGE-2 and MAGE-3 (Van der Bruggen et al., (1991) *Science,* 254:1643); CEA, TRP-1, TRP-2, P-15 and tyrosinase (Brichard et al., (1993) *J. Exp. Med.* 178:489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, adenocarcinoma, thymoma, lymphoma, sarcoma, lung cancer, liver cancer, colon cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer and others (see, e.g., Rosenberg, (1996) *Ann. Rev. Med.* 47:481-91).

Alternatively, the heterologous nucleotide sequence may encode any polypeptide that is desirably produced in a cell in vitro, ex vivo, or in vivo. For example, the parvovirus vectors may be introduced into cultured cells and the expressed gene product isolated therefrom.

It will be understood by those skilled in the art that the heterologous nucleotide sequence(s) of interest may be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements that are native to the target cell or subject to be treated are most preferred. Also preferred are promoters/enhancer elements that are native to the heterologous nucleic acid sequence. The promoter/enhancer element is chosen so that it will function in the target cell(s) of interest. Mammalian promoter/enhancer elements are also preferred. The promoter/enhance element may be constitutive or inducible.

Inducible expression control elements are preferred in those applications in which it is desirable to provide regulation over expression of the heterologous nucleic acid sequence(s). Inducible promoters/enhancer elements for gene delivery are preferably tissue-specific promoter/enhancer elements, and include muscle specific (including cardiac, skeletal and/or smooth muscle), neural tissue specific (including brain-specific), eye (including retina-specific and cornea-specific), liver specific, bone marrow specific, pancreatic specific, spleen specific, and lung specific promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein which the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

Gene Transfer Technology.

The parvovirus vectors according to the present invention also provide a means for delivering heterologous nucleotide sequences into a broad range of cells, including dividing and non-dividing cells. The parvovirus vectors may be employed to deliver a nucleotide sequence of interest to a cell in vitro, e.g., to produce a polypeptide in vitro or for ex vivo gene therapy. The vectors are additionally useful in a method of delivering a nucleotide sequence to a subject in need thereof, e.g., to express an immunogenic or therapeutic polypeptide. In this manner, the polypeptide may thus be produced in vivo in the subject. The subject may be in need of the polypeptide because the subject has a deficiency of the polypeptide, or because the production of the polypeptide in the subject may impart some therapeutic effect, as a method of treatment or otherwise, and as explained further below.

In general, the parvovirus vectors of the present invention may be employed to deliver any foreign nucleic acid with a biological effect to treat or ameliorate the symptoms associated with any disorder related to gene expression. Alternatively, the invention can be used to treat any disease state for which it is beneficial to deliver a therapeutic polypeptide. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), phospholamban, serca2a, zinc finger proteins that regulate the phospholamban gene, Barkct, β2-adrenergic receptor, β2-adrenergic receptor kinase (BARK), phosphoinositide-3 kinase (PI3 kinase), calsarcin, etc.), arthritis (insulin-like growth factors), joint disorders (insulin-like growth factors), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including RANKL and/or VEGF) can be administered with a bone allograph, for example, following a break or surgical removal in a cancer patient.

Alternatively, a gene transfer vector may be administered that encodes any other therapeutic polypeptide.

In particular embodiments, an AAV2-derived and/or AAV3b derived vector comprising the 263 and/or 265 mutations according to the present invention is used to deliver a nucleic acid of interest as described herein to a tumor or to skeletal muscle, cardiac muscle, astrocytes and/or glial cells, for example, to treat a disorder associated with any of these cells or tissues such as Parkinson's disease, astrocytomas, glioblastomas, muscular dystrophy, heart disease (including PAD and congestive heart failure), and the like.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus parvovirus vectors produced according to the methods of the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The parvovirus vectors according to the present invention may also be employed to provide an antisense nucleic acid or RNAi to a cell in vitro or in vivo. Expression of the antisense nucleic acid or RNAi in the target cell diminishes expression of a particular protein by the cell. Accordingly, antisense nucleic acids or RNAi may be administered to decrease expression of a particular protein in a subject in need thereof. Antisense nucleic acids or RNAi may also be administered to cells in vitro to regulate cell physiology, e.g., to optimize cell or tissue culture systems.

Further, the parvovirus vectors according to the instant invention find further use in diagnostic and screening methods, whereby a gene of interest is transiently or stably expressed in a cell culture system, or alternatively, a transgenic animal model. The invention can also be practiced to deliver a nucleic acid for the purposes of protein production, e.g., for laboratory, industrial or commercial purposes.

Delivery of Immunogenic Polypeptides.

As a further aspect, parvovirus vectors of the present invention may be used to produce an immune response in a subject. According to this embodiment, a parvovirus vector comprising a nucleotide sequence encoding an immunogen may be administered to a subject, and an active immune response is mounted by the subject against the immunogen. Immunogens are as described hereinabove. Preferably, a protective immune response is elicited.

Alternatively, the parvovirus vector may be administered to a cell ex vivo and the altered cell is administered to the subject. The heterologous nucleotide sequence is introduced into the cell, and the cell is administered to the subject, where the heterologous nucleotide sequence encoding the immunogen is preferably expressed and induces an immune response in the subject against the immunogen. In particular embodiments, the cell is an antigen presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

According to the foregoing methods of inducing an immune response in a subject, it is preferred that the parvovirus vector carrying the heterologous nucleotide sequence is administered in an immunogenically effective amount, as described herein.

The parvovirus vectors of the present invention may also be administered for cancer immunotherapy by administration of a parvovirus vector expressing cancer cell antigens (or an immunologically similar molecule) or any other immunogen that produces an immune response against a cancer cell. To illustrate, an immune response may be produced against a cancer cell antigen in a subject by administering a parvovirus vector comprising a heterologous nucleotide sequence encoding the cancer cell antigen, for example to treat a patient with cancer. The parvovirus vector may be administered to a subject in vivo or by using ex vivo methods, as described herein.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Preferred are methods of treating and preventing tumor-forming cancers.

The term "tumor" is also understood in the art, for example, as an abnormal mass of undifferentiated cells within a multicellular organism. Tumors can be malignant or benign. Preferably, the methods disclosed herein are used to prevent and treat malignant tumors.

Cancer cell antigens according to the present invention have been described hereinabove. By the terms "treating cancer" or "treatment of cancer," it is intended that the severity of the cancer is reduced or the cancer is prevented or at least partially eliminated. Preferably, these terms indicate that metastasis of the cancer is prevented or reduced or at least partially eliminated. It is further preferred that these terms indicate that growth of metastatic nodules (e.g., after surgical removal of a primary tumor) is prevented or reduced or at least partially eliminated. By the terms "prevention of cancer" or "preventing cancer" it is intended that the methods at least partially eliminate or reduce the incidence or onset of cancer. Alternatively stated, the onset of cancer in the subject may be slowed, controlled, decreased in likelihood or probability, or delayed.

In particular embodiments, cells may be removed from a subject with cancer and contacted with parvovirus particles according to the instant invention. The modified cell is then administered to the subject, whereby an immune response against the cancer cell antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., $\alpha$-interferon, $\beta$-interferon, $\gamma$-interferon, $\omega$-interferon, $\tau$-interferon, interleukin-1$\alpha$, interleukin-1$\beta$, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-$\alpha$, tumor necrosis factor-$\beta$, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the parvovirus vectors.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

Subjects, Pharmaceutical Formulations, and Modes of Administration.

Parvovirus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, non-human primates, bovines, ovines, caprines, equines, felines, canines, lagomorphs, etc. Human subjects include neonates, infants, juveniles, and adults. In particular embodiments, the subject has antibodies against one or more AAV (e.g., AAV serotypes such as AAV1 and/or AAV2). In other embodiments, the subject has previously been administered a different AAV vector (e.g., an immunologically distinct AAV). Optionally, the subject is "in need of" the methods of the present invention, e.g., because the subject has or is believed at risk for a disorder including those described herein or that would benefit from the delivery of a nucleic acid including those described herein.

In particular embodiments, the present invention provides a pharmaceutical composition comprising a virus particle or virus capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleotide sequence to a cell in vitro. The virus particles may be introduced to the cells at the appropriate multiplicity of infection according to standard transduction methods appropriate for the particular target cells. Titers of virus to administer can vary, depending upon the target cell type and number, and the particular virus vector, and can be determined by those of skill in the art without undue experimentation. Preferably, at least about $10^3$ infectious units, more preferably at least about $10^5$ infectious units are introduced to the cell.

The cell(s) to be introduced the parvovirus vector may be of any type, including but not limited to neural cells (including cells of the peripheral and central nervous systems, in particular, brain cells such as neurons, oligodendricytes, glial cells, astrocytes), lung cells, cells of the eye (including retinal cells, retinal pigment epithelium, and corneal cells), epithelial cells (e.g., gut and respiratory epithelial cells), muscle cells, dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

The parvovirus vectors may be introduced to cells in vitro for the purpose of administering the modified cell to a subject. In particular embodiments, the cells have been removed from a subject, the parvovirus vector is introduced therein, and the cells are then replaced back into the subject. Methods of removing cells from subject for treatment ex vivo, followed by introduction back into the subject are known in the art (see, e.g., U.S. Pat. No. 5,399,346; the disclosure of which is incorporated herein in its entirety). Alternatively, the recombinant parvovirus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the parvovirus vector are administered to the subject in a therapeutically effective amount in combination with a pharmaceutical carrier.

A "therapeutically effective" amount as used herein is an amount that is sufficient to provide some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

In some embodiments, cells that have been transduced with a parvovirus vector may be administered to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount that is sufficient to evoke an active immune response in the subject to which the pharmaceutical formulation is administered. Preferably, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the parvovirus particles or capsids of the invention to subjects. Administration of the parvovirus particles or capsids of the present invention to a human subject or an animal in need thereof can be by any means known in the art for administering virus vectors. Preferably, the parvovirus vector is delivered in a therapeutically effective dose in a pharmaceutically acceptable carrier.

The parvovirus vectors of the invention can further be administered to elicit an immunogenic response (e.g., as a vaccine). Typically, vaccines of the present invention comprise an immunogenically effective amount of virus in combination with a pharmaceutically acceptable carrier. Preferably, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the parvovirus particles to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular vector that is being used.

In particular embodiments, a chimeric vector according to the present invention that comprises a 263 and/or 265 mutation as described herein in an AAV2 or AAV3b backbone is administered to skeletal muscle, cardiac muscle and/or brain (e.g., to treat muscular dystrophy, heart disease (e.g., PAD or congestive heart failure), Parkinson's disease, astrocytomas, glioblastomas) or to a tumor.

Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation. Further, the virus particle can be delivered dried to a surgically implantable matrix such as a bone graft substitute, a suture, a stent, and the like (e.g., as described in U.S. Patent Publication No. US-2004-0013645-A1).

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The parvovirus vectors disclosed herein may be administered to the lungs of a subject by any suitable means, but are preferably administered by administering an aerosol suspension of respirable particles comprised of the parvovirus vectors, which the subject inhales. The respirable particles may be liquid or solid. Aerosols of liquid particles comprising the parvovirus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the parvovirus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLE 1

Triage Approach

Materials and Methods
Plasmid and DNA Mutagenesis

Figure 1A:
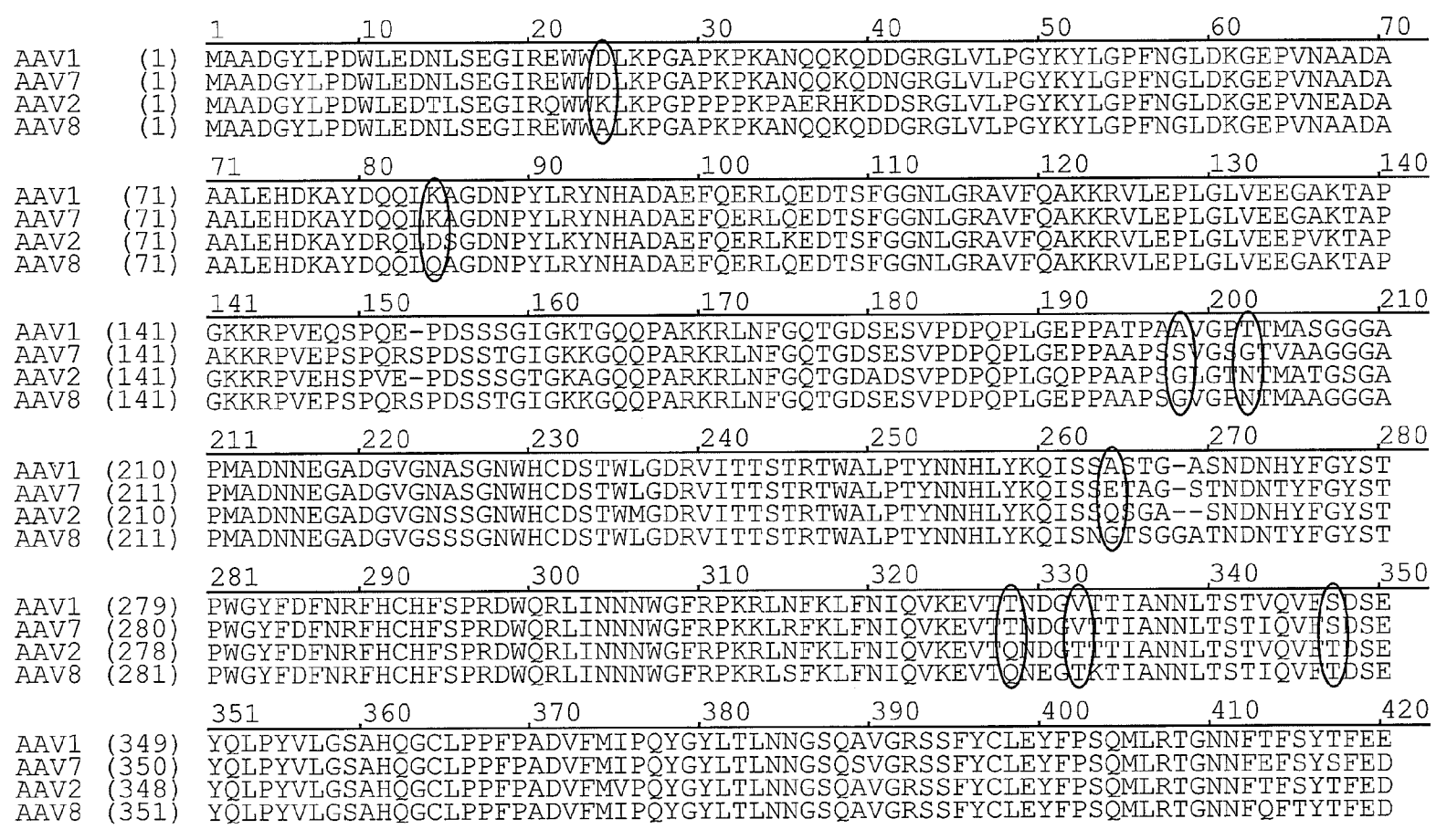
Figure 1B:
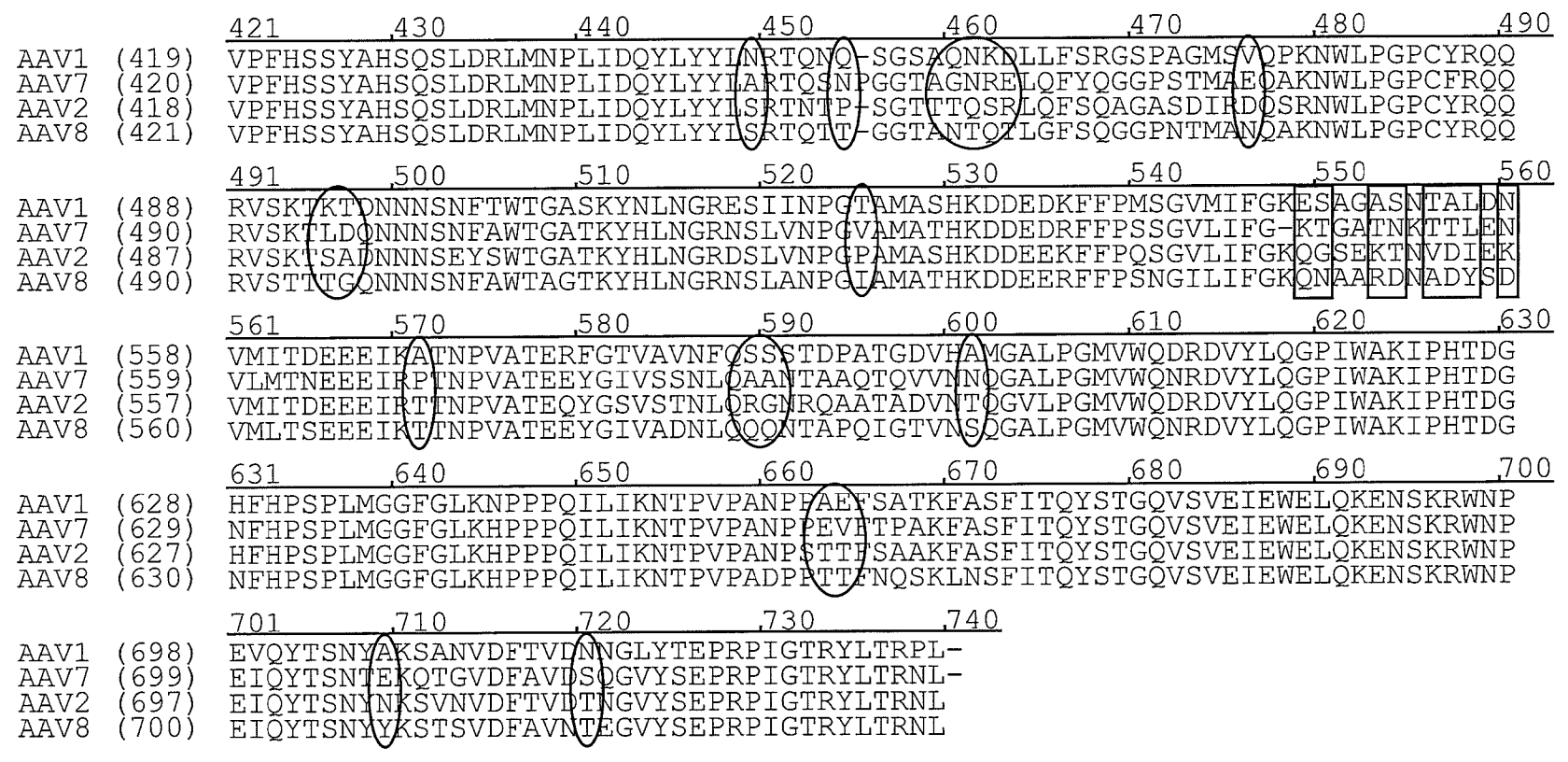

Starting plasmids for these experiments were pxr1, pxr2, prx3 (Rabinowitz et al, (2001) *J. Virology* 76:781-801). All plasmid mutagenesis was performed using either the Quik Change Multi Site Mutagenesis or the Quik Change Site Directed Mutagenesis kits (both from Stratagene). Accuracy of the nucleotide changes was verified by DNA sequence analyses followed by DNA subcloning to eliminate any unwanted artifacts generated by the mutagenesis approach. In certain instances, subcloning was performed using the newly generated mutant to generate another mutant.
Recombinant Virus Production All recombinant AAV (rAAV) viruses were generated using the standard triple transfection method (Haberman et al. 1999. Production of recombinant adeno-associated viral vectors and use in in vitro and in vivo administration, p. 4.17.1-4.17.25. In J. Crawley, et al. (eds.), Current protocols in neuroscience, vol. 1. John Wiley & Sons, Inc., New York, N.Y.). rAAV was purified in this study using standard cesium chloride gradients or using heparin column chromatography (Id.). The method used for virus purification is indicated in the corresponding figure. The physical titer of the different viral preparations was evaluated using dot blot hybridization. The preparations being compared in one experiment were evaluated on the same dot blots to control for variation between different dot blots.
Animal Imaging $1 \times 10^{10}$ viral genome containing particles (vg) were injected into the gastrocnemius of 6-week-old male BALB/c mice. A total of 6 limbs were injected for each virus type using 25 µl of virus. Animals were imaged at different days post injection using the Roper Scientific Imaging (Princeton Instruments). Briefly, animals were anesthetized and injected IP with luciferin substrate. Ten minutes post-injection the animals were placed in the chamber and light emission was determined. The average number of total pixels per region of interest was determined using the CMIR_Image software (Center for Molecular Imaging Research, Mass. General) and plotted over time.
Heparin Binding Experiments Batch binding of rAAV to heparin agarose was performed as described previously (Rabinowitz, (2004) *J. Virology* 78:4421-4432). Briefly, equivalent particles of rAAV virions were applied to heparin agarose type 1 (H-6508, Sigma, St. Louis, Mo.) in 1×PBS, allowed to bind for one hour at room temperature, centrifuged at low speed for 2 minutes, and supernatant (flow through) was removed. Six washes of five bed-volumes of PBS 1 mM $MgCl_2$ were performed, followed by a three-step elution of five bed-volumes of PBS 1 mM $MgCl_2$ containing 0.5 M NaCl (step 1), 1.0 M NaCl (step 2), or 1.5 M NaCl (step 3). The number of rAAV particles present in the washes and the 3-step elution was determined by dot blot hybridization.
Results
Rationale of the Triage Approach It is clear in the literature that different serotypes of AAV exhibit differing abilities to transduce different tissues. One well-documented example is the ability of AAV1 to preferentially transduce skeletal muscle. The amino acid sequences of AAV1 and AAV2 are 83% identical. One previous study exchanged large regions of the AAV2 capsid with the corresponding amino acids of AAV1 and examined the ability of the resultant vectors to transduce skeletal muscle (Hauck et al., (2003) *J. Virology* 77:2768-2774). They identified 2 amino acids that appeared to confer enhanced skeletal muscle transduction by AAV2, albeit not as well as AAV1. The present studies examined the phenomenon in a more detailed manner. Employing bio-informatic and structure-function analysis, key amino acids residues in the AAV capsid proteins were identified that account for enhanced AAV1 transduction for testing in the context of majority AAV2 capsid. This approach avoids the need to make all the different changes of amino acids between the 2 serotypes and all of the different permutations. Further, this approach took advantage of the crystal structure of AAV2, amino acid sequence alignments, and known properties of the various AAV serotypes. Alignments were generated of these very similar capsid proteins from the different serotypes. Amino acids in common between AAV1 and AAV7 capsid proteins and distinct from AAV2 and AAV8 capsid proteins were identified. Thirty-six amino acid candidates were identified via this triage approach (FIG. 1A). Based on modeling of the crystal structure, the 12 best candidates were chosen to test for enhanced muscle transduction (FIG. 1B).

Some AAV Variants Exhibited No Difference from AAV2 while Others are Much Better than AAV2.

Figure 2B:
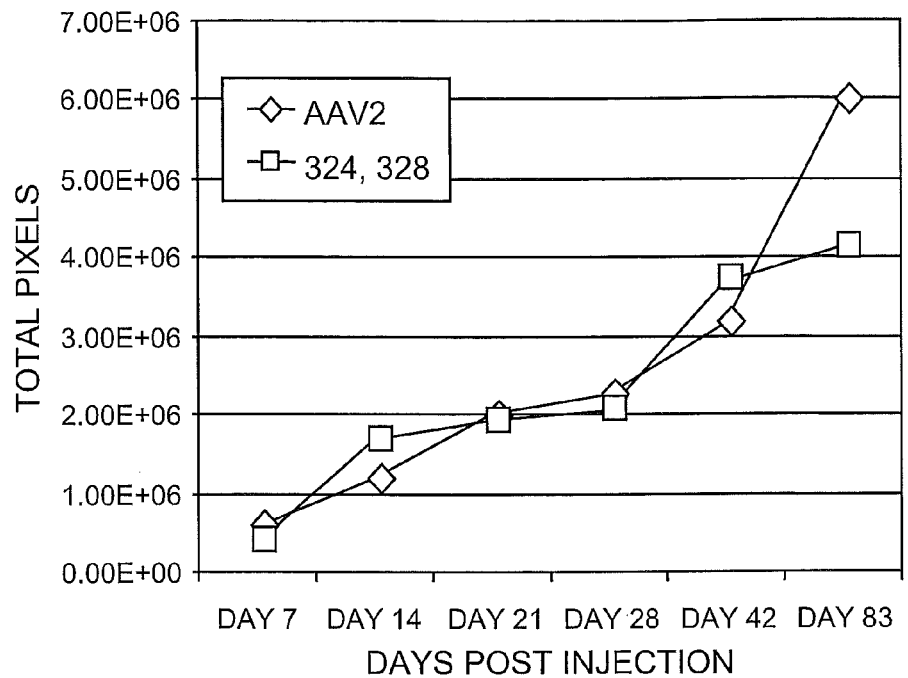
FIG. 2B. Quantitation of light emission from muscle of AAV2 versus 324, 328 variant. The amount of light emitted from the experiment depicted in FIG. 2A was calculated using CMIR_image software. The regions of interest (ROI) from each leg were defined and used to calculate total photons emitted. Data is represented as an average of all 6 limbs.

The different AAV variants were evaluated for their ability to transduce skeletal muscle following injection of $1\times10^{10}$ genome containing viral particles into the gastrocnemius muscle of BALB/c mice. Some virus variants did not exhibit any difference in the capability to transduce skeletal muscle (FIGS. 2a and b). Although the 324, 328 positions are located on loops predicted to lie on the capsid surface, changing of these amino acids to the corresponding amino acids in AAV1 did nothing to improve the capability of this virus to transduce skeletal muscle (FIGS. 2A and 2B).

Figure 3A:
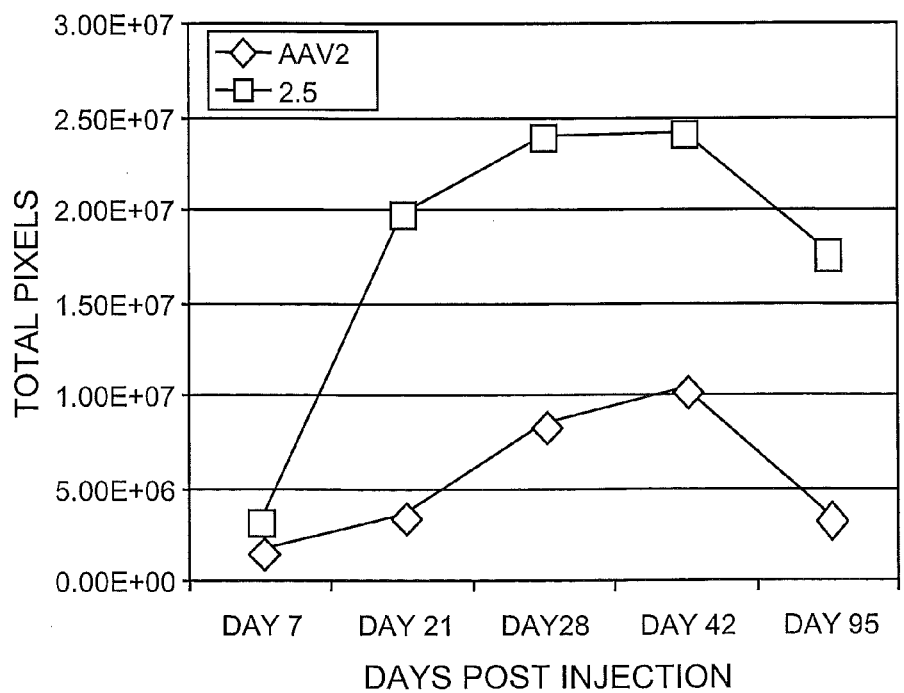
FIG. 3A. Changing the amino acids of AAV2 to create the 2.5 variant greatly enhanced the muscle tropism of this variant. $1 \times 10^{10}$ viral genome-containing particles were injected into each gastrocnemius of male Balb/c mice. Each mouse was imaged at 7, 14, 28, 42, and 95 days post injection. The virus used in this experiment was purified using heparin HPLC. The amount of light emitted from each animal was calculated using CMIR_image software. The regions of interest (ROI) from each leg were defined and used to calculate total photons emitted. Data is represented as an average of all 6 limbs.
Figure 3B:
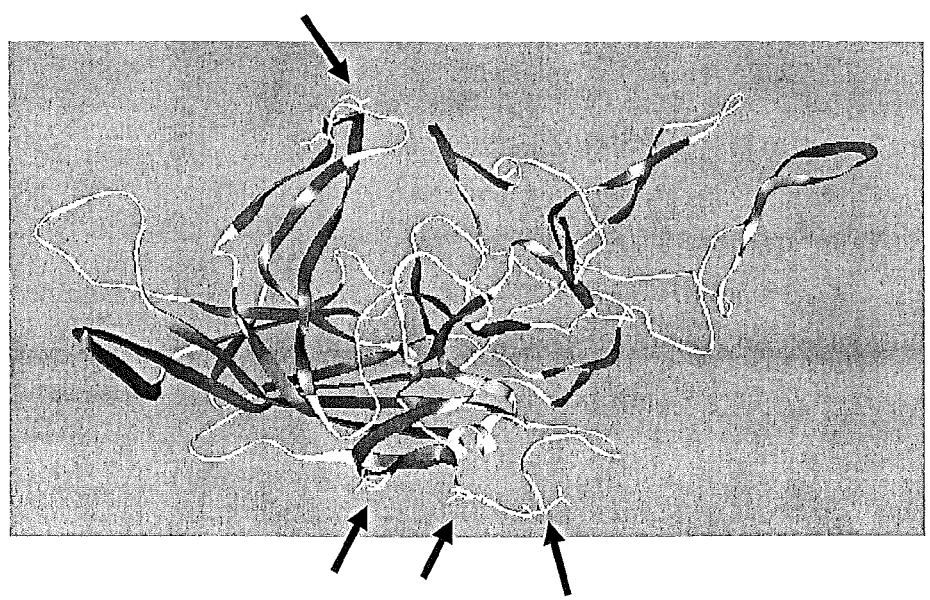
FIG. 3B. Locations of the amino acid positions on the AAV2 capsid monomer. Depicted is a 3D ribbon structure of the AAV2 capsid monomer. The locations of the changes made in the 2.5 variant are indicated by arrows. The top arrow points to the 263, 265 regions, and the 3 bottom arrows point to the 709, 712, 720 amino acids.
Figure 3C:
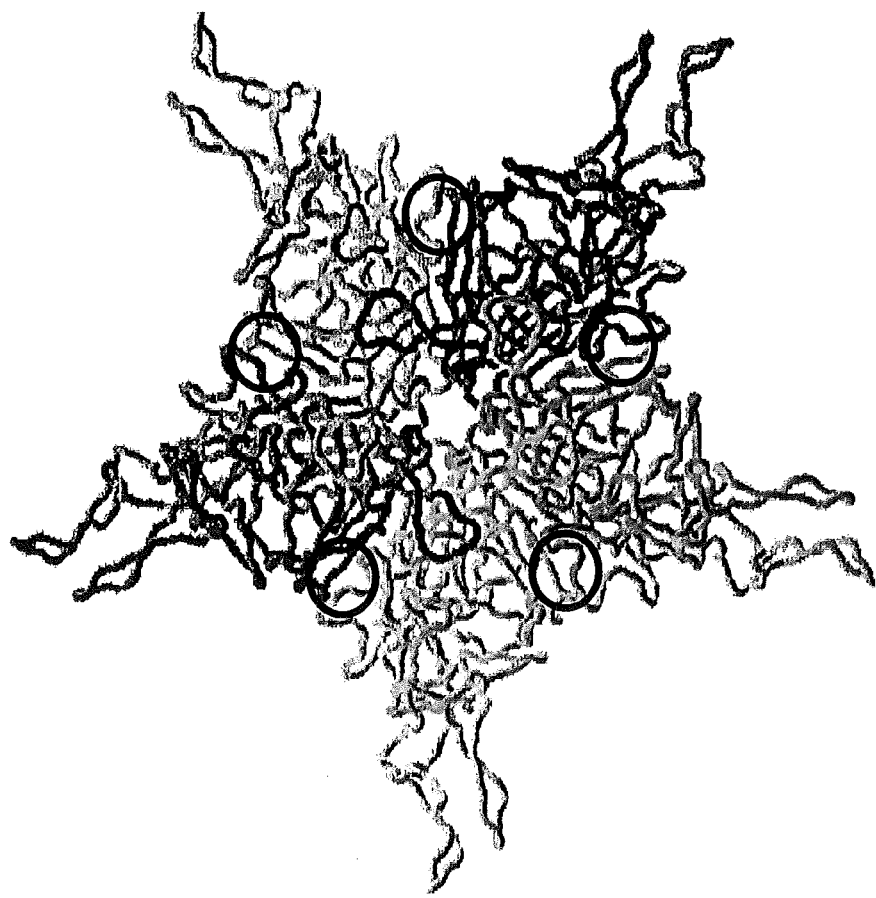
FIG. 3C. The position of the 2.5 amino acids on the AAV2 pentamer. The location of the 2.5 variant amino acids is indicated by the circle. Although 2 of the amino acids lie on one portion of the individual subunit and 3 other amino acids lie on another portion of the same subunit, when 2 subunits come together to form the AAV capsid, these 5 amino acids lie in very close proximity at the 2-fold axis of symmetry.

One variant (2.5) exhibited much higher muscle transduction than AAV2 (FIG. 3A). This variant had 5 amino acid changes that were located in the 2-fold axis of symmetry (FIG. 3B). Although it appears that groups of these 5 amino acids lie on different parts of the same subunit (2 on one side and 3 on another), they are in very close proximity when 2 of the subunits come together (FIG. 3C).

Figure 5:
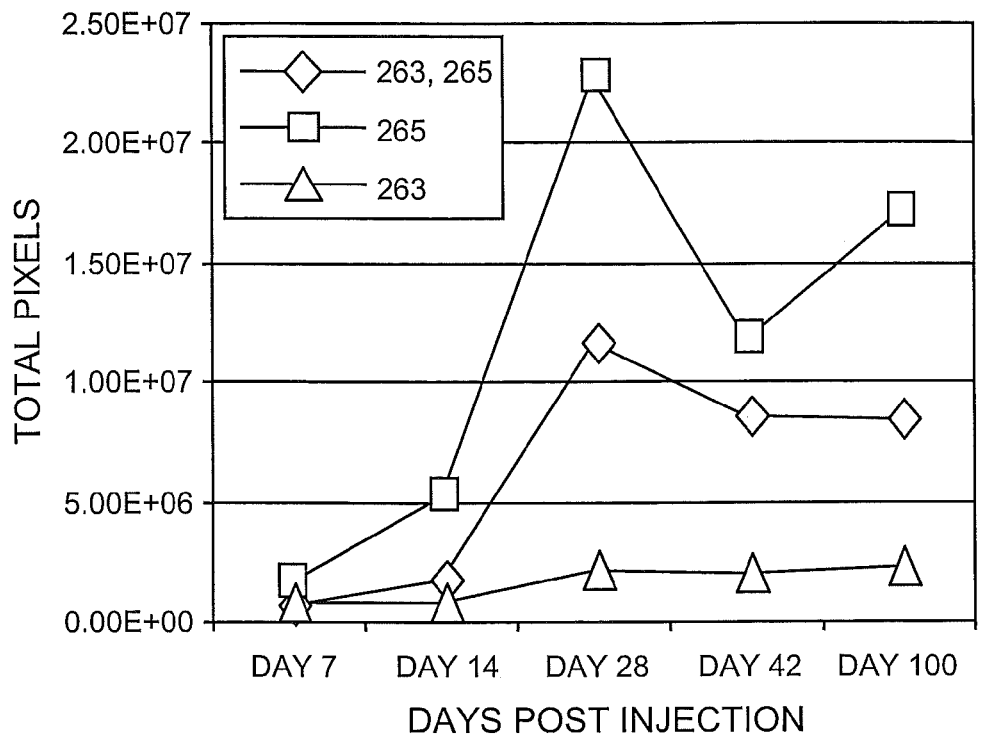
FIG. 5. The threonine insertion at position 265 is responsible for the majority of the enhanced muscle tropism of 2.5. Subsets (263 or 265) of the 263, 265 variant were generated. $1 \times 10^{10}$ viral genome-containing particles were injected into each gastrocnemius of male Balb/c mice. Each mouse was imaged at 7, 14, 28, 42, and 100 days post injection. The virus used in this experiment was purified using cesium chloride gradients. The 265 variant exhibited enhanced muscle tropism similar to the 263, 265 variant whereas the 263 variant did not exhibit enhanced muscle tropism.

To investigate whether all 5 amino acids were necessary for this enhanced muscle tropism we made the 263, 265 variants as well as the 709, 712, 720 variants. These variants were tested in similar imaging experiments (FIG. 4). The 709, 712, 720 variant exhibited a muscle transduction similar to AAV2, while the 263, 265 variant exhibited an enhanced muscle transduction similar to what was observed with the 2.5 variant containing all 5 amino acid changes. A 263 and a separate 265 variant were constructed and tested in similar experiments (FIG. 5). These experiments revealed that the amino acid mostly responsible for enhanced AAV1 transduction is located at the 265 position. This is essentially an insertion of a threonine in the AAV2 capsid sequence.

The same insertion has been made at positions 263 and 265 in the AAV3b backbone (FIG. 10).

Figures 7, 8:
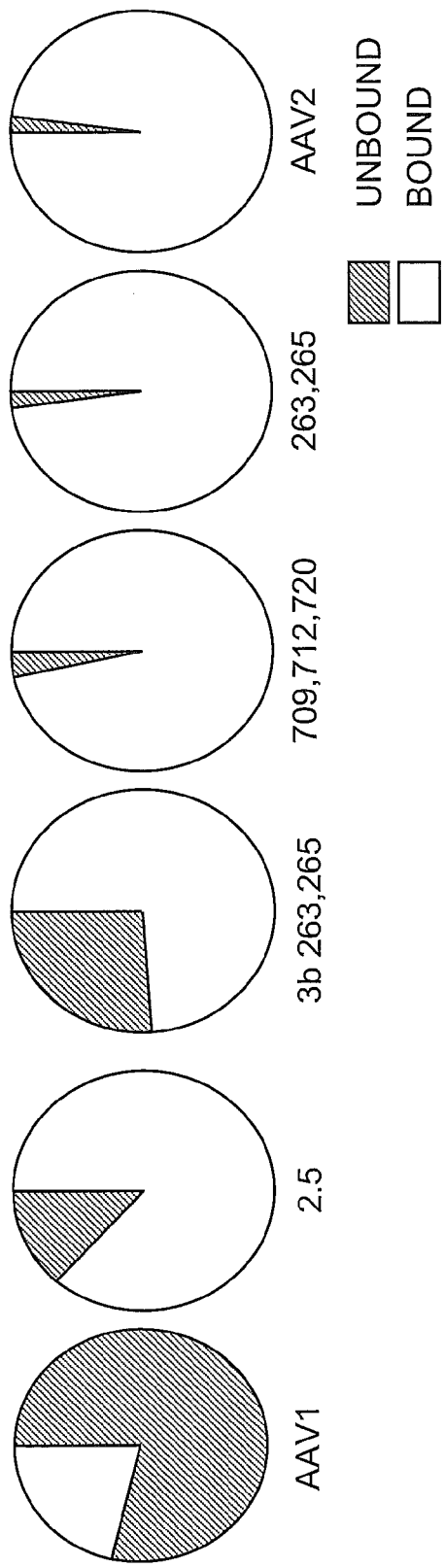
FIG. 7. Identification of the 263, 265 region of other AAV serotypes as an area of natural insertions. The capsid sequences of AAV serotypes 1 (SEQ ID NO:5), 2 (SEQ ID NO:6), 3a (SEQ ID NO:7), 3b (SEQ ID NO:7), 4 (SEQ ID NO:8), 5 (SEQ ID NO:9), 6 (SEQ ID NO:5), 7 (SEQ ID NO:10), 8 (SEQ ID NO:11) and 9 (SEQ ID NO:12) were subjected to multiple sequence alignment using the Align program in the Vector NTI software package. Shown in the box are the amino acids of the other serotypes corresponding to the amino acids identified in AAV1 as responsible for enhanced muscle tropism.
FIG. 8. Heparin binding profile of AAV variants. Equivalent particles of each AAV variant were applied to heparin agarose type 1 and allowed to bind. The columns were washed with PBS, followed by elution in sodium chloride. The number of particles present in the flow thru, washes and elutions were determined via dot blot hybridization. Data is depicted as percentage of unbound particles (wash and flow thru) and bound (elution).

Interestingly, the 263, 265 region is divergent amongst the serotypes (FIG. 7 boxed region). There are additional amino acid insertions in this area compared to AAV2.

Figure 6:
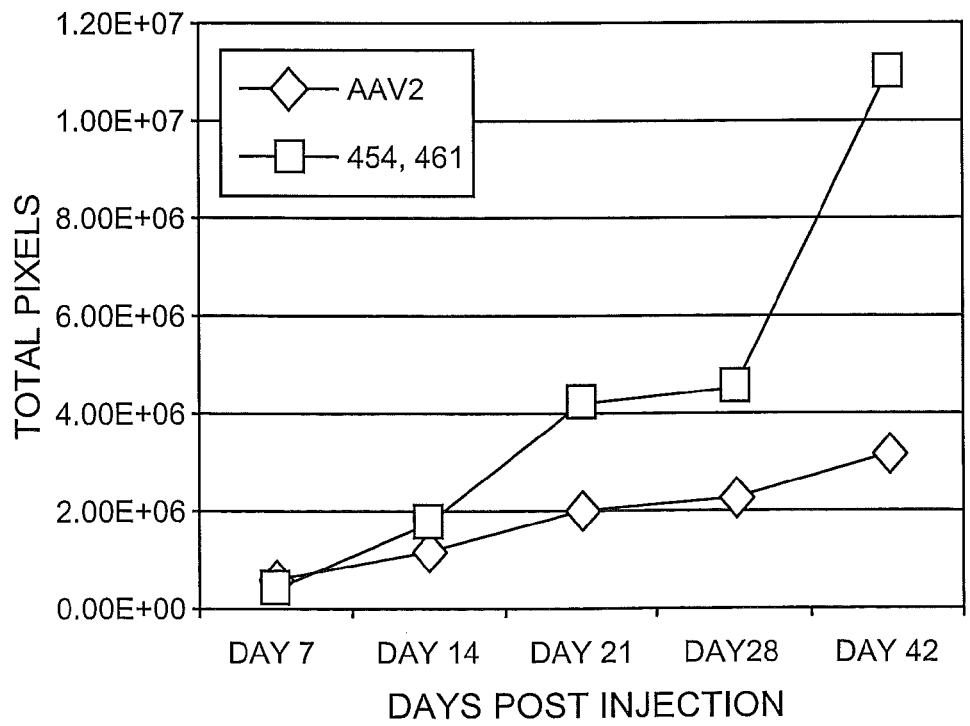
FIG. 6. The 454, 461 variant exhibited enhanced muscle tropism at later time points post injection. $1 \times 10^{10}$ viral genome-containing particles of AAV2 or 454, 461 were injected into each gastrocnemius of male Balb/c mice. Each mouse was imaged at 7, 14, 21, 28, and 42 days post injection. The virus used in this experiment was purified using cesium chloride gradients. 454, 461 muscle transduction was similar to AAV2 at early time points (day 7 and 14) but expression was better than AAV2 at later time points (days 21-42).

Another variant that exhibits higher muscle transduction than AAV2 is the 454, 461 variant (FIG. 6). Different combinations of 265 with the 454, 461 changes are assessed to determine whether further enhancement can be observed by combining these variants.

Finally, we examined the ability of the different variants to be purified by heparin (FIG. 8). All of the variants tested exhibited heparin binding profiles similar to AAV2.

EXAMPLE 2

Immunological Profile

Similar to other non-enveloped viruses, high doses of AAV generate neutralizing antibody that prevents repeated dosing. With the advent of new serotypes, repeat administration is possible. To explore the ability to avoid a pre-existing immune response to AAV2, the chimeric 2.5 vector was tested for transgene expression in vitro after exposure to serum from animals pre-exposed to different AAV serotypes (1, 2, and 2.5 respectively).

To generate animals with a robust immune response to AAV virion shell, $4\times10^{10}$ particles of AAV serotype 1, 2, and 2.5 vector were independently injected intramuscularly in C57blk6 mice. Four weeks post-injection, blood was isolated and serum collected. Serum from these animals was than used in a neutralizing antibody assay using 293 cells and AAV specific serotype vectors expressing GFP as a reporter gene. In this assay, serum is sequentially diluted and than mixed with a known amount of serotype specific vector ($1\times10^{8}$ particles) at 4° C. for 2 hr. This mixture of serum and vector is then added to 293 cells in 24-well plates in the presence of adenovirus helper virus at a multiplicity of infection of 5. Under these conditions, green fluorescent protein (GFP) expression is a measure of serotype-specific vector ability to infect cells in the presence of neutralizing antibodies. The neutralizing antibody titer is then calculated as the highest dilution where GFP expression is 50% or less than control vector (without pre-mixture with serotype specific serum).

As seen in Table 3, animals pre-exposed to AAV1 could neutralize AAV 1 GFP transduction with dilutions as high as 1:1000. However this serotype 1 specific neutralizing antibody required more mouse serum to neutralize AAV chimeric 2.5 (1:100 dilution). More importantly, this observation was true for mouse sera obtained from animals pre-exposed to AAV serotype 2 virion shells. In this assay, only after sera were diluted 1:10,000 was observe 50% GFP transduction observed when compared to AAV2 control. However, for chimeric 2.5, 50% GFP transduction was observed with only 1:100 dilution of this mouse serum. Since only 0.6% of the amino acid changes differ from AAV2 in this chimeric vector, these alterations had profound effects on the ability of pre-existing AAV2 neutralizing antibody to recognize the AAV 2.5 capsid shell. Animals pre-exposed to 2.5 and then assayed for neutralizing activity against AAV 1, 2, and 2.5 yielded expected results (see Table 3) with highest dilution required for the 2.5 vector (1:8000) followed by 1:1000 for AAV 2 and 1:100 for AAV serotype 1 respectively. The conclusion from these studies is that the 5 amino acid alteration in chimeric 2.5 although small in number (0.6% total amino acids) was sufficient to significantly affect the immune profile for this virion when challenged with neutralizing antibodies specific for AAV2.

Based on these studies, the 2.5 vector would be suitable for transducing individuals pre-exposed to AAV1, AAV2 or both, thereby providing greater versatility in available vectors. For example, this chimeric vector would allow for re-administration in animals and patients pre-exposed to AAV2. In addition, this chimeric vector demonstrates that selected amino acids can be changed in the AAV2, amino acid capsid sequence that significantly alter immune response. Based on these results, similar alterations at similar capsid coding regions for other AAV serotypes would also result in unique immune profiles allowing one to easily generate a large number of alternative AAV variants for repeat administration without having to change to a new serotype capsid each time.

TABLE 3

The Neutralizing Antibody Assay for AAV2.5 virus

| Sera | Target virus | NA titer |
|---|---|---|
| AAV1 | AAV1 | 1:1000 |
|  | AAV2.5 | 1:100 |
| AAV2 | AAV2 | 1:10000 |
|  | AAV2.5 | 1:100 |
| AAV2.5 | AAV1 | 1:100 |
|  | AAV2 | 1:1000 |
|  | AAV2.5 | 1:8000 |

EXAMPLE 3

Figure 12:
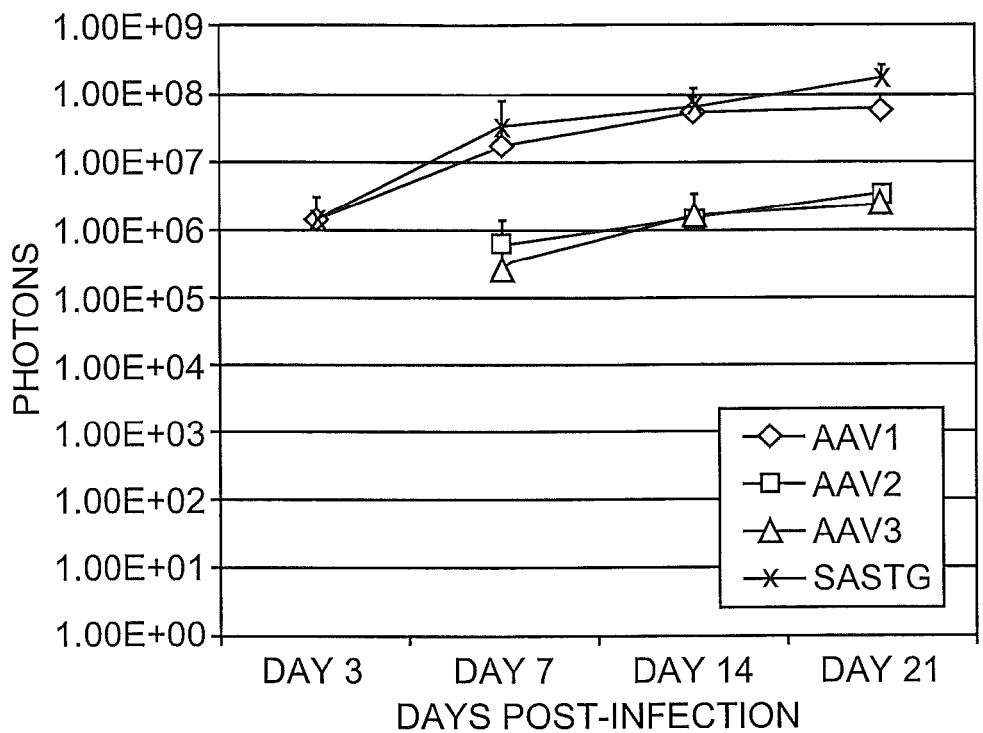
FIG. 12. Luciferase activity over time (days 3, 7, 14 and 21) in mice injected with equivalent genome containing particles ($1\times10^{10}$) of AAV1, AAV2, AAV3b, or SASTG as determined by in vivo live animal imaging.

263, 265 Mutations in an AAV3b Backbone (SASTG) Confers Enhanced Skeletal Muscle Transduction These amino acids (263, 265) from AAV1 were also engineered into the corresponding positions of the AAV3b capsid, a serotype closely related to AAV2 and one that also does not transduce skeletal muscle well, to generate a vector designated as SASTG. Mice were injected with equivalent genome containing particles ($1 \times 10^{10}$) of AAV1, AAV2, AAV3b, or SASTG and were assessed for luciferase activity over time (days 3, 7, 14, and 21) using in vivo live animal imaging (FIG. 12).

As expected, both AAV2 and AAV3 do not transduce skeletal muscle as efficiently as AAV1. Expression from the AAV2 and AAV3b injected mice could not be detected at day 3; whereas expression from AAV1 and, importantly, from SASTG could be detected at day 3. The expression pattern of SASTG paralleled that of AAV1 at all time points post injection rather than its AAV3b parent.

EXAMPLE 4

Transduction of Brain and Liver

Figure 13:
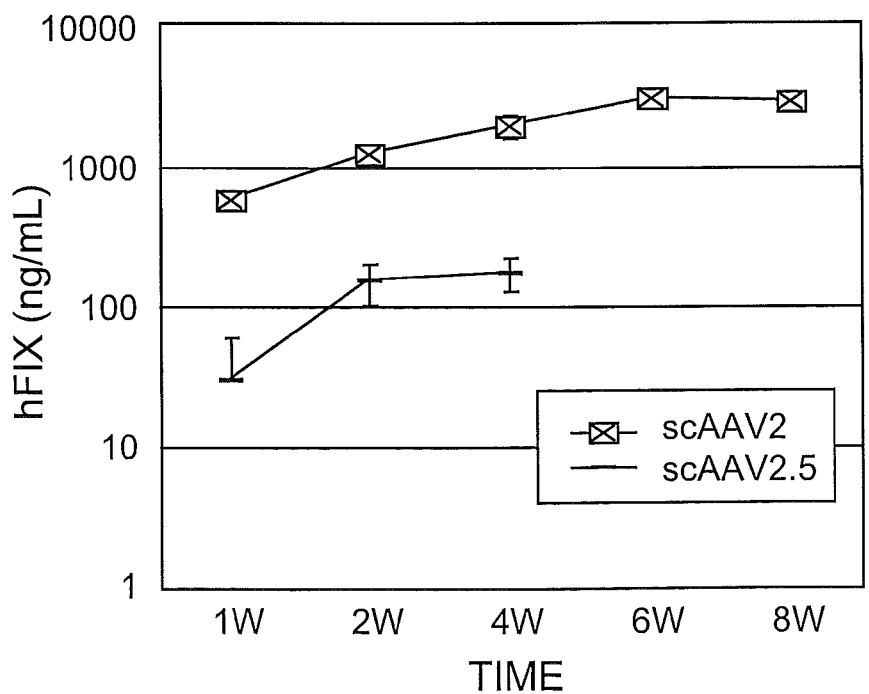
FIG. 13. Human Factor IX (hFIX) levels detected by ELISA in sera from mice treated with an AAV2 or chimeric 2.5 vector carrying the hFIX transgene.

Six- to eight-week-old male C57bl/6 mice were utilized to determine efficiency of AAV2 and the 2.5 vector transduction in liver. The mice were anesthetized using 300 μL 2.5% Avertin, and $1 \times 10^{11}$ particles of AAV2 and 2.5 vector carrying the human Factor IX (hFIX) transgene virus were dissolved in 250 μL PBS and injected slowly through the portal vein. The vectors were duplexed virus particles as described in international patent publication WO 01/92551. After 1 and 6 weeks, 100 μL of blood from each mouse was collected from the tail vein using heparin-coated capillary glass tubes. Serum was collected by centrifuging the blood sample at 4° C., 8000 rpm for 20 min. Sera were stored at −80° C. until tested. Expression of hFIX in the serum was tested by standard ELISA methods. Serial dilutions of normal human serum with hFIX levels of 5 μg/mL were used as a standard. Using this assay, it was found that the 2.5 vector has a reduced ability to transduce liver as compared with the parent AAV2 virus (FIG. 13). This experiment demonstrates that in addition to gaining muscle tropism, the 2.5 vector has lost liver specific tropism characteristic of AAV2.

Figure 14:
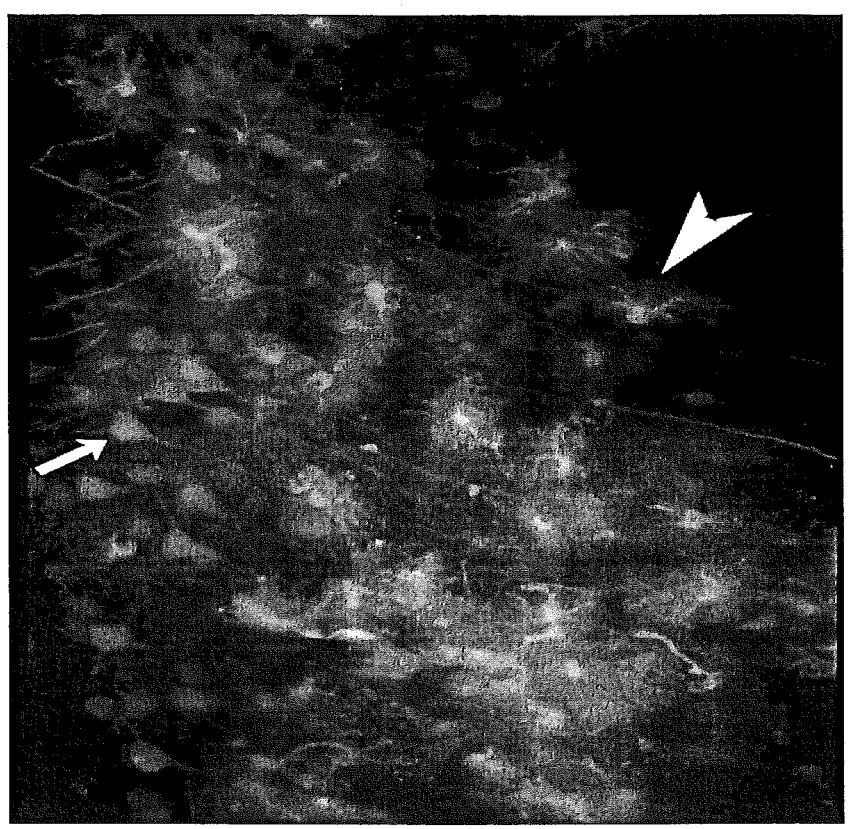
FIG. 14. Green fluorescent protein (GFP) transgene expression in neuronal (left arrow) and non-neuronal (right arrow) cells in the cortex of mouse brain after administration of a chimeric 2.5 vector carrying the GFP transgene.

In another experiment, the duplexed 2.5 vector was injected into the cortex region of the mouse brain (FIG. 14) using a green fluorescent protein (GFP) reporter transgene cassette and conditions previously established for AAV 2 and assayed for neuron specific transduction. It is well-established that AAV1 and AAV2 are specific for neuronal transduction. As shown in FIG. 14, the 2.5 vector transduces neurons (arrow on the left) as well as non-neuronal cells (arrow on right). Based on morphology, these cells appear to be astrocytes.

The sum of these experiments when testing the 2.5 vector for tissue-specific transduction in vivo demonstrates that in addition to gaining tissue-specific tropism (e.g., muscle, skeletal or cardiac derived from the AAV serotype 1 parent), and losing cell type specific transduction (e.g., liver-hepatocyte-specific transduction of recipient AAV2), these vectors have gained a new tropism (non-neuronal/astrocytes) that is not present in either the donor parent (AAV1) or recipient parent capsid (AAV2) and is totally unique to the chimeric 2.5 vector.

The foregoing is illustrative of the present invention, and is not to be construed as limiting thereof. The invention is defined by the following claims, with equivalents of the claims to be included therein.

That which is claimed is:

1. A method of administering a nucleic acid to a cell comprising contacting the cell with a chimeric virus vector comprising:
   a) a chimeric adeno-associated virus (AAV) capsid comprising a selective amino acid insertion immediately following amino acid position 264 in an AAV2 capsid subunit having the amino acid sequence of (SEQ ID NO:3) or a corresponding change in another AAV capsid subunit; and
   b) a nucleic acid comprising an AAV terminal repeat sequence and a heterologous nucleic acid sequence,
   wherein the nucleic acid is packaged within the chimeric AAV capsid.

2. A method of delivering a nucleic acid to a subject comprising administering to the subject a chimeric virus vector comprising:
   a) a chimeric adeno-associated virus (AAV) capsid comprising a selective amino acid insertion immediately following amino acid position 264 in an AAV2 capsid subunit having the amino acid sequence of (SEQ ID NO:3) or a corresponding change in another AAV capsid subunit; and
   b) a nucleic acid comprising an AAV terminal repeat sequence and a heterologous nucleic acid sequence,
   wherein the nucleic acid is packaged within the chimeric AAV capsid.

3. The method of claim 2, wherein the subject is a human subject.

4. The method of claim 2, wherein the subject has or is at risk for a disorder selected from the group consisting of a muscular dystrophy including Duchenne or Becker muscular dystrophy, hemophilia A, hemophilia B, multiple sclerosis, diabetes mellitus, Gaucher disease, Fabry disease, Pompe disease, cancer, arthritis, muscle wasting, heart disease including congenital heart failure or peripheral artery disease, intimal hyperplasia, a neurological disorder including epilepsy, Huntington's disease, Parkinson's disease or Alzheimer's disease, an autoimmune disease, cystic fibrosis, thalassemia, Hurler's disease, Krabbe's disease, phenylketonuria, Batten's disease, spinal cerebral ataxia, LDL receptor deficiency, hyperammonemia, anemia, arthritis, a retinal degenerative disorder including macular degeneration, adenosine deaminase deficiency, and cancer including tumor-forming cancers.

5. The method of claim 2, wherein the chimeric virus vector or pharmaceutical formulation is administered to skeletal muscle.

6. The method of claim 5, wherein the subject has or is at risk for muscular dystrophy.

7. The method of claim 5, wherein the chimeric virus vector comprises a chimeric AAV capsid comprising a selective amino acid insertion following amino acid position 264 in an AAV2 capsid subunit.

8. The method of claim 5, wherein the chimeric virus vector comprises a chimeric AAV capsid comprising a selective amino acid insertion following amino acid position 264 in an AAV3b capsid subunit.

9. The method of claim 2, wherein the chimeric virus vector or pharmaceutical formulation is administered to cardiac muscle.

10. The method of claim 9, wherein the subject has or is at risk for heart disease.

11. The method of claim 10, wherein the subject has or is at risk for congestive heart failure or peripheral artery disease.

12. The method of claim 10, wherein the chimeric virus vector comprises a chimeric AAV capsid comprising a selective amino acid insertion following amino acid position 264 in an AAV3b capsid subunit.

13. The method of claim 2, wherein the chimeric virus vector or pharmaceutical formulation is administered to glial cells and/or astrocytes.

14. The method of claim 13, wherein the subject has or is at risk for Parkinson's Disease, astrocytomas or glioblastoma.

15. The method of claim 13, wherein the chimeric virus vector comprises a chimeric AAV capsid comprising a selective amino acid insertion following amino acid position 264 in an AAV2 capsid subunit.

* * * * *

UNITED STATES PATENT AND TRADEMARK OFFICE
CERTIFICATE OF CORRECTION

PATENT NO.       : 9,012,224 B2
APPLICATION NO.  : 12/983547
DATED            : April 21, 2015
INVENTOR(S)      : Bowles et al.

Page 1 of 1

It is certified that error appears in the above-identified patent and that said Letters Patent is hereby corrected as shown below:

In The Specification

Column 22, Line 47: Please correct "$10^6$ to/ml," to read -- $10^6$ tu/ml, --

Column 22, Line 49: Please correct "$10^8$ to/ml," to read -- $10^8$ tu/ml, --

Column 22, Lines 49 and 50: Please correct "$10^9$ to/ml," to read -- $10^9$ tu/ml, --

Signed and Sealed this
Nineteenth Day of January, 2016

Michelle K. Lee
*Director of the United States Patent and Trademark Office*